(12) United States Patent
Harris, III et al.

(10) Patent No.: US 7,531,577 B2
(45) Date of Patent: May 12, 2009

(54) ARYLSULFONAMIDYL TETRALIN DERIVATIVES AND USES THEREOF

(75) Inventors: Ralph New Harris, III, Redwood City, CA (US); James M. Kress, Raleigh, NC (US); David Bruce Repke, Milpitas, CA (US); Russell Stephen Stabler, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/820,681

(22) Filed: Jun. 20, 2007

(65) Prior Publication Data

US 2008/0015208 A1 Jan. 17, 2008

Related U.S. Application Data

(60) Provisional application No. 60/815,493, filed on Jun. 20, 2006.

(51) Int. Cl.
*C07C 311/21* (2006.01)
*C07D 233/48* (2006.01)
*C07D 239/14* (2006.01)
*A61K 31/18* (2006.01)

(52) U.S. Cl. .................. 514/595; 564/56; 564/57; 564/82; 564/92; 544/332; 546/153; 548/331.5; 548/490

(58) Field of Classification Search ............ None
See application file for complete search history.

(56) References Cited

U.S. PATENT DOCUMENTS

| | | | |
|---|---|---|---|
| 5,137,901 A | 8/1992 | Junge et al. |
| 5,374,643 A | 12/1994 | Atwal et al. |
| 5,412,117 A | 5/1995 | Koga et al. |
| 5,614,633 A | 3/1997 | Koga et al. |
| 5,627,138 A | 5/1997 | Anderson et al. |
| 5,646,308 A | 7/1997 | Koga et al. |
| 5,663,194 A | 9/1997 | Mewshaw |
| 5,719,182 A | 2/1998 | Cousins et al. |
| 5,739,135 A | 4/1998 | Biller et al. |
| 5,869,478 A | 2/1999 | Ding et al. |
| 5,874,446 A | 2/1999 | Koga et al. |
| 5,883,099 A | 3/1999 | Biller et al. |
| 5,935,958 A | 8/1999 | Kozlowski et al. |
| 5,977,167 A | 11/1999 | Koga et al. |
| 6,083,982 A | 7/2000 | Wechter et al. |
| 6,150,402 A | 11/2000 | Wechter et al. |
| 6,214,881 B1 | 4/2001 | Xiang |
| 6,310,107 B1 | 10/2001 | Kato et al. |
| 6,448,243 B1 | 9/2002 | Kitazawa et al. |
| 6,479,536 B1 | 11/2002 | Ohkawa et al. |
| 6,559,144 B2 | 5/2003 | Diefenbach et al. |
| 6,586,475 B1 | 7/2003 | Kato et al. |
| 6,605,632 B1 | 8/2003 | Lesieur et al. |
| 6,613,805 B2 | 9/2003 | Kato et al. |
| 6,638,972 B2 | 10/2003 | Kelly et al. |
| 6,660,752 B2 | 12/2003 | O'Connor et al. |
| 6,706,757 B2 | 3/2004 | Greenblatt et al. |
| 6,784,314 B2 | 8/2004 | Yamashita et al. |
| 2002/0002177 A1 | 1/2002 | Cousins et al. |
| 2004/0024210 A1 | 2/2004 | Johansson et al. |
| 2004/0077867 A1 | 4/2004 | Kato et al. |
| 2004/0087577 A1 | 5/2004 | Pratt et al. |
| 2004/0097492 A1 | 5/2004 | Pratt et al. |
| 2004/0162285 A1 | 8/2004 | Pratt et al. |
| 2004/0167123 A1 | 8/2004 | Pratt et al. |
| 2005/0075331 A1 | 4/2005 | Pratt et al. |
| 2005/0154053 A1 | 7/2005 | Rhijn et al. |
| 2006/0069094 A1 | 3/2006 | Bonhaus et al. |
| 2006/0167255 A1 | 7/2006 | Greenhouse et al. |
| 2008/0146567 A1* | 6/2008 | Kolczewski et al. ...... 514/235.2 |

FOREIGN PATENT DOCUMENTS

| | | |
|---|---|---|
| EP | 0 488 616 A1 | 6/1992 |
| EP | 0 587 180 A2 | 3/1994 |
| EP | 0 747 374 B1 | 12/1996 |
| WO | WO 97/02259 A1 | 1/1997 |
| WO | WO 98/00412 A1 | 1/1998 |
| WO | WO 01/85172 A1 | 5/2003 |
| WO | WO 03/059356 A2 | 7/2003 |
| WO | WO 03/099801 A1 | 12/2003 |
| WO | WO 2004/000828 A1 | 12/2003 |
| WO | WO 2004/058150 A2 | 7/2004 |
| WO | WO 2005/040355 A2 | 5/2005 |
| WO | WO 2006/040180 | * 4/2006 |

OTHER PUBLICATIONS

Dhanak, D., et al., "Identification and Biological Characterization of Heterocyclic Inhibitors of the Hepatitis C Virus RNA-dependent RNA Polymerase," *J. Biological Chem.* (2002) vol. 277, No. 41, pp. 38322-38327.

(Continued)

*Primary Examiner*—Fiona T Powers
(74) *Attorney, Agent, or Firm*—Robert C. Hall

(57) ABSTRACT

Compounds of the formula I:

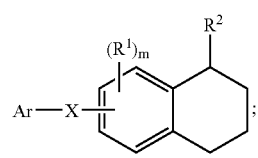

or pharmaceutically acceptable salts thereof, wherein Ar, X, m, $R^1$, $R^2$ are as defined herein. Also provided are methods for preparing, compositions comprising, and methods for using compounds of formula I for treatment of 5-HT6-mediated diseases.

4 Claims, No Drawings

OTHER PUBLICATIONS

Gu, B., et. al., "Arresting Initiation of Hepatitis C Virus RNA Synthesis Using Heterocyclic Derivatives," *J. Biological Chem.* (2003) vol. 278, No. 19, pp. 16602-16607.

Nguyen, T. T., et. al. "Resistance Profile of a Hepatitis C Virus RNA-Dependent RNA Polymerase Benzothiadiazine Inhibitor," *Antimicrobial Agents and Chemo.* (2003) vol. 47, No. 11, pp. 3525-3530.

* cited by examiner

ARYLSULFONAMIDYL TETRALIN DERIVATIVES AND USES THEREOF

CROSS REFERENCE TO RELATED APPLICATIONS

This application is entitled to the benefit of provisional patent application Ser. No. 60/815,493 filed on Jun. 20, 2006, the disclosure of which is incorporated herein by reference.

FIELD OF THE INVENTION

This invention relates to arylsulfonamidyl naphthalene compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nervous system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory in Alzheimer's patients), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin I D Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

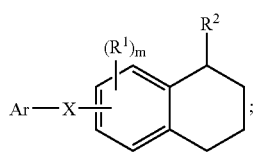

or a pharmaceutically acceptable salt thereof, wherein:
m is from 0 to 3;
Ar is optionally substituted aryl or optionally substituted heteroaryl;
X is $-SO_2-NR^g-$ or $-NR^g-SO_2-$ wherein $R^g$ is hydrogen or alkyl, or $R^g$ forms an alkylene bridge connecting to Ar, or $R^g$ forms an alkylene bridge connecting to Ar;
each $R^1$ is independently halo, alkyl, haloalkyl, alkoxy, hydroxy, heteroalkyl, cyano, $-S(O)_t-R^a$, $-C(=O)-NR^bR^c$, $SO_2-NR^bR^c$, $-N(R^d)-C(=O)-R^e$, or $-C(=O)-R^e$, where t is from 0 to 2, $R^a$, $R^b$, $R^c$, $R^d$ and $R^e$ each independently is hydrogen or alkyl, and $R^f$ is hydrogen, alkyl, alkoxy or hydroxy;
$R^2$ is

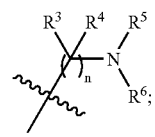

n is from 1 to 3;
$R^3$ and $R^4$ each independently is hydrogen or alkyl, or $R^3$ and $R^4$ together may form $=O$ or $=NR^f$ wherein $R^f$ is hydrogen or alkyl;
one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or $R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or one of $R^5$ and $R^6$ and one of $R^3$ and $R^4$ together with the atoms to which they are attached may form a five- or six-membered ring that optionally includes an additional heteroatom selected from O, N and S.

The invention also provides methods for preparing, methods of using, and pharmaceutical compositions comprising the aforementioned compounds.

DETAILED DESCRIPTION OF THE INVENTION

The invention provides arylsulfonamidyl tetralin compounds, associated compositions, methods for use as therapeutic agents, and methods of preparation thereof.

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Antagonist" refers to a compound that diminishes or prevents the action of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms (i.e., "$C_1$-$C_6$alkyl"). Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkylcarbonyl" means a group of the formula —C(O)—R wherein R is alkyl as defined herein.

"Alkylcarbonylaminoalkyl" means a group of the formula —R—NR'—R" wherein R is alkylene, R' is hydrogen or alkyl, and R" is alkylcarbonyl as defined herein.

"Alkylsulfonyl" means a group —SO$_2$—R wherein R is alkyl as defined herein.

"Alkylsulfonylalkyl" means a group —R—SO$_2$—$R^1$ wherein $R^1$ is alkyl and R is alkylene as defined herein.

"Alkylsulfonylalkylaminoalkyl" means a group of the formula —R—NR'—R" wherein R is alkylene, R' is hydrogen or alkyl, and R" is alkylsulfonylalkyl as defined herein.

"Alkylsulfonamidoalkyl" means a group of the formula —R—NR'—SO$_2$—R" wherein R is alkylene, R' is hydrogen or alkyl, and R" is alkyl as defined herein.

"Alkoxy" means a group —OR, wherein R is alkyl as defined herein. Examples of alkoxy moieties include, but are not limited to, methoxy, ethoxy, isopropoxy, and the like.

"Alkoxycarbonyl" means a group of the formula —C(O)—R wherein R is alkoxy as defined herein.

"Alkoxycarbonylaminoalkyl" means a group of the formula —R—NR'—R" wherein R is alkylene, R' is hydrogen or alkyl, and R" is alkoxycarbonyl as defined herein.

"Alkoxycarbonylalkyl" means a group of the formula —R—C(O)—R' wherein R' is alkoxy and R is alkylene as defined herein.

"Alkoxycarbonylalkylaminoalkyl" means a group of the formula —R—NR'—R" wherein R is alkylene, R' is hydrogen or alkyl, and R" is alkoxycarbonyl alkyl as defined herein.

"Alkoxyalkyl" is a group of the formula —R—OR' wherein R' is alkyl and R is alkylene as defined herein.

"Alkoxyalkylaminoalkyl" means a group of the formula —R—NR'—R" wherein R is alkylene, R' is hydrogen or alkyl, and R" is alkoxyalkyl as defined herein.

"Amino" means a group —NRR' wherein R and R' each independently is hydrogen or alkyl as defined herein. "Amino" thus includes "alkylamino" and "dialkylamino".

"Amidinyl" means a group of the formula:

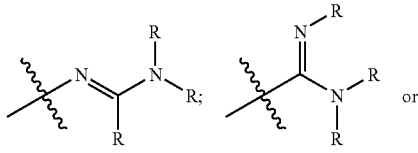 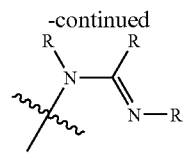

-continued

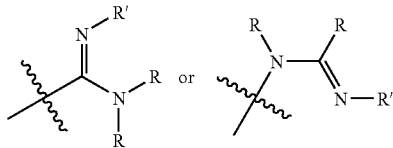

wherein each R independently is hydrogen or alkyl as defined herein. "N-cyanoamidinyl" means a group of the formula wherein R' is cyano and R is hydrogen or alkyl as defined herein.

"Aminosulfonyl" means a group —SO$_2$—R wherein R is —NR'— and R' is hydrogen or alkyl as defined herein.

"Amidinylalkyl" means a group —R—R' wherein R' is amidinyl and R is alkylene as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Alkylaminoalkyl" means a group of the formula —R—NR'—R" wherein R' is hydrogen or alkyl, R" is alkyl, and R is alkylene as defined herein. "Dialkylaminoalkyl" is alkylaminoalkyl wherein R' is alkyl.

"Aminocarbonyl" means a group of the formula —C(O)—R wherein R is amino as defined herein.

"Aminocarbonylalkyl" means a group of the formula —R—C(O)—R' wherein R' is amino and R is alkylene as defined herein.

"Aminocarbonylalkylaminoalkyl" means a group of the formula —R—NR'—R" wherein R is alkylene, R' is hydrogen or alkyl, and R" is aminocarbonylalkyl as defined herein.

"Aminoalkylcarbonyl" means a group of the formula —C(O)—R—R' wherein R' is amino and R is alkylene as defined herein.

"Aminoalkylcarbonylaminoalkyl" means a group of the formula —R—NR'—R" wherein R is alkylene, R' is hydrogen or alkyl, and R" is aminocarbonylalkyl as defined herein.

"Aminosulfonamidoalkyl" means a group of the formula —R—NR'—SO$_2$—R" wherein R is alkylene, R' is hydrogen or alkyl, and R" is amino as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, naphthalenyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. Preferred aryl are phenyl and naphthyl, which may be optionally substituted as defined herein.

"Arylene" means a divalent aryl radical wherein aryl is as defined herein.

"Arylene" includes, for example, ortho-, meta- and para-phenylene (1,2-phenylene, 1,3-phenylene and 1,4-phenylene respectively), which may be optionally substituted as defined herein.

"Arylalkyl" and "Aralkyl", which may be used interchangeably, mean a radical —R—R' where R is an alkylene group and R' is an aryl group as defined herein; e.g., benzyl, phenylethyl, 3-(3-chlorophenyl)-2-methylpentyl, and the like are examples of arylalkyl.

"Cycloalkyl" means a saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

"Cycloalkylalkyl" means a moiety of the formula —R—R', where R is alkylene and R' is cycloalkyl as defined herein.

"Guanidinyl" means a group of the formula

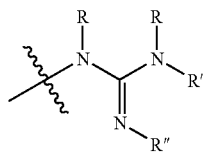

wherein each R independently is hydrogen or alkyl, R' is hydrogen, alkyl, or phenyl, and R" is hydrogen, alkyl or cyano. The phenyl moiety of "guanidinyl" may be optionally substituted as defined herein. "N-cyanoguanidinyl" means R" in the formula for guanidinyl is cyano.

"Guanidinylalkyl" is a group —R—R' wherein R' is guanidinyl and R is alkylene as defined herein. "N-cyanoguanidinylalkyl" means R' is N-cyanoguanidinyl as defined herein.

"Guanidinylcarbonylalkyl" means a group of the formula —R—C(O)—R' wherein R' is guanidinyl and R is alkylene as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is O, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, methoxy, ethoxy, 2-hydroxyethyl, 3-hydroxypropyl, 2-methoxyethyl, 3-methoxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic monovalent radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyridinyl, pyridazyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof. The aforementioned heteroaryl moieties may be partially saturated. Thus, "heteroaryl" includes "imidazolinyl", tetrahydropyrimidinyl" and the like. Preferred heteroaryl include pyridinyl, pyrimidinyl, thienyl and pyrrolyl.

"Heteroarylene" means a divalent heteroaryl radical wherein heteroaryl is as defined herein. "Heteroarylene" may be optionally substituted as defined herein. "Heteroarylene" includes, for example, indolylene, pyrimidinylene, and the like.

"Heteroarylaminoalkyl" means a group of the formula —R—NR'—R" wherein R is alkylene, R' is hydrogen or alkyl, and R" is heteroaryl as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, piperidinyl, piperazinyl, homopiperazinyl, azepinyl, pyrrolidinyl, pyrazolidinyl, imidazolinyl, imidazolidinyl, pyridinyl, pyridazinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like, including partially unsaturated derivatives thereof.

"Hydroxyalkyl" means an alkyl as defined herein that is substituted one, two or three times with hydroxy.

"Hydroxyalkylcarbonyl" means a group of the formula —C(O)—R—OH wherein R is alkylene as defined herein.

"Hydroxyalkylcarbonylaminoalkyl" means a group of the formula —R—NR'—R" wherein R is alkylene, R' is hydrogen or alkyl, and R" is hydroxyalkylcarbonyl as defined herein.

"Hydroxyalkylaminoalkyl" means a group of the formula —R—NR'—R" wherein R is alkylene, R' is hydrogen or alkyl, and R" is hydroxyalkyl as defined herein.

"Imidazolinyl" means a group of the formula

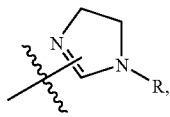

and more preferably a group of the formula

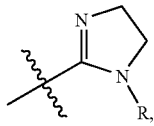

wherein R is hydrogen or alkyl. "Imidazolinyl" may be interchangeably used with "4,5-dihydro-1H-imidazol-2-yl".

"Imidazolonyl" means a group of the formula

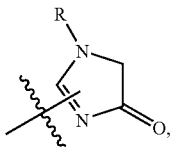

and more preferably a group of the formula

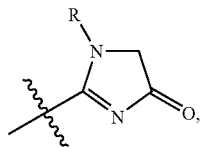

wherein R is hydrogen or alkyl.

"Imidazolonylaminoalkyl means a group of the formula —R—NR'—R" wherein R is alkylene, R' is hydrogen or alkyl, and R" is imidazolonyl as defined herein.

"Imidazolinylalkyl" means a group —R—R' wherein R' is imidazolinyl as defined herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Imidazolylcarbonyl" means a group of the formula

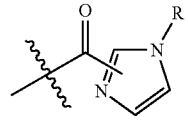

wherein R is hydrogen or alkyl as defined herein.

"Imidazolinylaminoalkyl" means a group of the formula —R—NR'—R" wherein R is alkylene, R' is hydrogen or alkyl, and R" is imidazolinyl as defined herein.

"Imidazolylaminoalkyl" means a group of the formula —R—NR'—R" wherein R is alkylene, R' is hydrogen or alkyl as defined herein, and R" is imidazolyl.

"Imidazolinylalkyl" is a group of the formula —R—R" wherein R is alkylene and R" is imidazolinyl as defined herein "Imidazolinylcarbonylaminoalkyl" means a group of the formula —R—C(O)—NR'—R" wherein R is alkylene, R' is hydrogen or alkyl, and R" is imidazolinyl as defined herein.

"Pyrimidinylaminoalkyl" means a group —R—R'—R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Pyrrolylcarbonyl" means a group of the formula

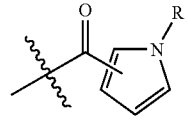

wherein R is hydrogen or alkyl as defined herein.

"Pyrrolylcarbonylaminoalkyl" means a group of the formula —R—NR'—R" wherein R is alkylene, R' is hydrogen or alkyl, and R" is pyrrolylcarbonyl as defined herein.

"Pyrrolidinylcarbonyl" means a group of the formula

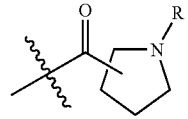

wherein R is hydrogen or alkyl as defined herein.

"Pyrrolidinylcarbonylaminoalkyl" means a group of the formula —R—NR'—R" wherein R is alkylene, R' is hydrogen or alkyl, and R" is pyrrolidinylcarbonyl as defined herein.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—NR'—R" wherein R" is tetrahydropyrimidinyl, R' is hydrogen or alkyl, and R is alkylene as defined herein.

"Urea" or "ureyl", which may be used interchangeably, means a group of the

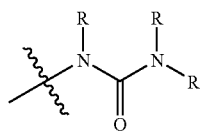

wherein each R is independently is hydrogen or alkyl.

"Urealkyl" means a group R—R' wherein R' is urea and R is alkylene as defined herein.

"Optionally substituted", when used in association with "aryl", phenyl", "heteroaryl", or "heterocyclyl", means an aryl, phenyl, heteroaryl, or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl. Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base.

Acceptable organic bases include diethanolamine, ethanolamine, N-methylglucamine, triethanolamine, tromethamine, and the like.

Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" pl-92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "aminoprotecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Those skilled in the art know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v. 4.0, a Beilstein Institute computerized system for the generation of IUPAC systematic nomenclature.

Chemical structures shown herein were prepared using ISIS® version 2.2. Any open valency appearing on a carbon, oxygen or nitrogen atom in the structures herein indicates the presence of a hydrogen.

Compounds of the Invention

The invention provides compounds of the formula I:

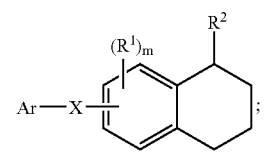

or a pharmaceutically acceptable salt thereof, wherein:
m is from 0 to 3;
Ar is optionally substituted aryl or optionally substituted heteroaryl;
X is $-SO_2-NR^k-$ or $-NR^g-SO_2-$ wherein $R^g$ is hydrogen or alkyl, or $R^k$ forms an alkylene bridge connecting to Ar, or $R^g$ forms an alkylene bridge connecting to Ar;
each R' is independently halo, alkyl, haloalkyl, alkoxy, hydroxy, heteroalkyl, cyano, $-S(O)_t-R^a$, $-C(=O)-NR^bR^c$, $-SO_2-NR^bR^c$, $-N(R^d)-C(=O)-R^e$, or $-C(=O)-R^e$, where t is from 0 to 2, $R^a$, $R^b$, $R^c$, $R^d$ and $R^e$ each independently is hydrogen or alkyl, and $R^f$ is hydrogen, alkyl, alkoxy or hydroxy;
$R^2$ is

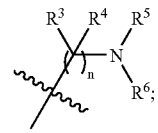

n is from 1 to 3;
$R^3$ and $R^4$ each independently is hydrogen or alkyl, or $R^3$ and $R^4$ together may form =O or =$NR^f$ wherein $R^f$ is hydrogen or alkyl;
one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; alkylsulfonylalkyl; or optionally substituted heteroaryl; or
$R^5$ and $R^6$ together with the nitrogen to which they are attached may form an amidinyl group, a urea group, a guanidinyl group or a five- or six-membered heteroaryl or heterocyclyl ring that is optionally substituted and which optionally includes an additional heteroatom selected from O, N and S; or
one of $R^5$ and $R^6$ and one of $R^3$ and $R^4$ together with the atoms to which they are attached may form a five- or six-membered ring that optionally includes an additional heteroatom selected from O, N and S.

It should be understood that the scope of this invention encompasses not only the various isomers which may exist but also the various mixture of isomers which may be formed.

Furthermore, the scope of the present invention also encompasses solvates and salts of compounds of formula I:

In certain embodiments of formula I, X is —$SO_2$—$NR^k$— and is located at the 6- or 7-position (with respect to $R^2$) of the tetralin ring system.

In certain embodiments of formula I, X is —$SO_2$—$NR^k$— and is located at the 6-position (with respect to $R^2$) of the tetralin ring system.

In certain embodiments of formula I, X is —$NR^g$—$SO_2$— and is located at the 6- or 7-position (with respect to $R^2$) of the tetralin ring system.

In certain embodiments of formula I, X is —$NR^g$—$SO_2$— and is located at the 6-position (with respect to $R^2$) of the tetralin ring system.

In certain embodiments of formula I, $R^k$ is hydrogen.

In certain embodiments of formula I, $R^g$ is hydrogen.

In certain embodiments of formula I, $R^g$ forms a $C_2$ or $C_3$ alkylene bridge to Ar In certain embodiments of the invention, the subject compounds may be of the formula IIa or formula IIb:

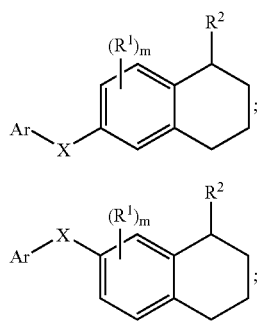

wherein m, Ar, X, $R^1$ and $R^2$ are as defined herein.

In many embodiments of formula I, formula IIa or formula IIb, m is 0 or 1. In certain embodiments of formula I, formula IIa or formula IIb, $R^1$ is halo.

In certain embodiments of formula I, formula Ia or formula IIb, m is 0 or 1 and $R^1$ is located at the 8-position of the tetralin ring system.

In certain embodiments of formula I, formula IIa or formula IIb, n is 1.

In certain embodiments of formula I, formula IIa or formula IIb, n is 2.

In certain embodiments of formula I, formula IIa or formula IIb, n is 3.

In certain embodiments of formula I, formula IIa or formula IIb, $R^3$ and $R^4$ are hydrogen.

In certain embodiments of formula I, formula IIa or formula IIb, X is —$SO_2$—NH—.

In certain embodiments of formula I, formula IIa or formula IIb, X is —NH—$SO_2$—.

In certain embodiments of formula I, formula IIa or formula IIb, X is —$NR^g$—$SO_2$— and $R^k$ forms an alkylene bridge with Ar.

In certain embodiments of formula I, formula IIa or formula IIb, one of $R^5$ and $R^6$ is hydrogen and the other is alkyl.

In certain embodiments of formula I, formula IIa or formula IIb, $R^5$ and $R^6$ are hydrogen.

In certain embodiments of formula I, formula IIa or formula IIb, one of $R^5$ and $R^6$ is hydrogen or alkyl and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula I, formula IIa or formula IIb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, formula IIa or formula IIb, one of $R^5$ and $R^6$ is hydrogen or alkyl and the other is: hydrogen; alkyl; alkylcarbonyl or aminocarbonyl.

In certain embodiments of formula I, formula IIa or formula IIb, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, formula IIa or formula IIb, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula I, formula IIa or formula IIb, one of $R^5$ and $R^6$ is hydrogen and the other is heteroaryl selected from pyrimidinyl, benzothiazol-2-yl, and 5,5-dimethyl-1,4,5,6-tetrahydropyrim In certain embodiments of formula I, formula IIa or formula IIb, $R^5$ and $R^6$ together with the nitrogen to which they are attached form an amidinyl group.

In certain embodiments of formula I, formula IIa or formula IIb, $R^5$ and $R^6$ together with the nitrogen to which they are attached form a guanidinyl group.

In certain embodiments of formula I, formula IIa or formula IIb, $R^5$ and $R^6$ together with the nitrogen to which they are attached form a urea group.

In certain embodiments of formula I, formula IIa or formula IIb, $R^3$ and $R^4$ together with the nitrogen to which they are attached form =$NR^f$ wherein $R^f$ is hydrogen.

In certain embodiments of formula I, formula IIa or formula IIb, $R^3$ and $R^4$ together with the nitrogen to which they are attached form =O.

In certain embodiments of formula I, formula IIa or formula IIb, one of $R^5$ and $R^6$ and one of $R^3$ and $R^4$ together with the atoms to which they are attached form an imidazolinyl ring.

In certain embodiments of formula I, formula IIa or formula IIb, $R^5$ and $R^6$ together with the nitrogen to which they are attached form or a five- or six-membered heteroaryl ring that is optionally substituted and which optionally includes an additional nitrogen heteroatom.

In certain embodiments of formula I, formula IIa or formula IIb, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula I, formula IIa or formula IIb, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula I, formula IIa or formula IIb, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula I, formula IIa or formula IIb, Ar is optionally substituted phenyl.

In certain embodiments of formula I, formula IIa or formula IIb, Ar is phenyl optionally substituted once or twice with halo, alkoxy, alkyl or haloalkyl.

In certain embodiments of formula I, formula IIa or formula IIb, Ar is 2-halophenyl or 3-halopheny.

In certain embodiments of formula I, formula IIa or formula IIb, Ar is heteroaryl.

In certain embodiments of formula I, formula IIa or formula IIb, Ar is heteroaryl selected from indolyl, pyrrolyl, imidazolyl, pyrazolyl, benzimidazolyl, thienyl, furanyl, pyridinyl and pyrimidinyl, each optionally substituted.

In certain embodiments of formula I, formula IIa or formula IIb, Ar is heteroaryl selected from indolyl, pyrrolyl, imidazolyl, pyrazolyl, and benzimidazolyl, each optionally substituted.

In certain embodiments of formula I, formula IIa or formula IIb, Ar is heteroaryl selected from indol-3-yl, pyrrol-3-yl, 1-methylimidazol-2-yl, imidazol-2-yl, pyrazol-4-yl, benzimidazol-4-yl, 6-fluoroindol-3-yl, 1-methylpyrrol-3-yl and 6-fluorobenzimidazol-4-yl.

In certain embodiments of formula I, formula IIa or formula IIb, one of $R^5$ and $R^6$ and one of $R^3$ and $R^4$ together with the atoms to which they are attached form an imidazolinyl ring.

In certain embodiments of formula I, formula IIa or formula IIb, m is 0 or 1, n is 1, and Ar is optionally substituted phenyl.

In certain embodiments of formula I, formula IIa or formula IIb, m is 0 or 1, n is 1, Ar is optionally substituted phenyl, and X is —SO$_2$—NH— or —NH—SO$_2$—.

In certain embodiments of formula I, formula IIa or formula IIb, m is 0 or 1, n is 1, Ar is optionally substituted phenyl, and X is —SO$_2$—NH—.

In certain embodiments of formula I, formula IIa or formula IIb, m is 0 or 1, n is 1, Ar is optionally substituted phenyl, and X is —NH—SO$_2$—.

In certain embodiments of formula I, formula IIa or formula IIb, m is 0 or 1, n is 1, and X and Ar together form:

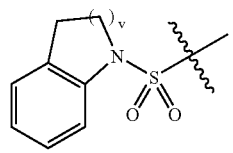

wherein v is 1 or 2.

In certain embodiments of formula I, formula IIa or formula IIb, m is 0 or 1, n is 1, Ar is optionally substituted phenyl, X is —SO$_2$—NH— or —NH—SO$_2$—, and $R^3$ and $R^4$ are hydrogen.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen or alkyl, and the other is: alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen and the other is alkyl.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen and the other is: hydrogen; alkyl; alkylcarbonyl; or aminocarbonyl.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen and the other is alkylcarbonyl.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen and the other is aminocarbonyl.

In certain embodiments of formula I, formula IIa or formula IIb, m is 0 or 1, n is 1, Ar is optionally substituted phenyl, X is —SO$_2$—NH—, and $R^2$ is aminomethyl wherein the amino is optionally substituted once with methyl, acetyl or aminocarbonyl.

In certain embodiments of formula I, formula IIa or formula IIb, m is 0 or 1, n is 1, Ar is optionally substituted phenyl, X is —SC)$_2$—NH— or —NH—SO$_2$—, and $R^2$ is: aminoalkyl; alkylaminoalkyl; dialkylaminoalkyl; imidazolinylaminoalkyl; imidazolinylalkyl, guanidinylalkyl; tetrahydropyrimidinylaminoalkyl; amidinylalkyl; urealkyl; amidinyl; heteroarylaminoalkyl; imidazolylaminoalkyl; guanidinylcarbonylalkyl; imidazolonylaminoalkyl; imidazolinylcarbonylaminoalkyl; aminocarbonylalkyl; pyrrolylcarbonylaminoalkyl; aminoalkylcarbonylaminoalkyl; alkoxycarbonylalkylaminoalkyl; N-cyanoguanidinylalkyl; alkylcarbonylaminoalkyl; aminocarbonylalkylaminoalkyl; pyrrolidinylcarbonylaminoalkyl; alkylsulfonamidoalkyl; aminosulfonamidoalkyl; alkoxycarbonylaminoalkyl; hydroxyalkylcarbonylaminoalkyl; hydroxyalkylaminoalkyl; alkoxyalkylaminoalkyl; or alkylsulfonylalkylaminoalkyl.

In certain embodiments of formula I, formula IIa or formula IIb, m is 0 or 1, and $R^2$ is: aminoalkyl; alkylaminoalkyl; dialkylaminoalkyl; guanidinylalkyl; amidinylalkyl; urealkyl; amidinyl; guanidinylcarbonylalkyl; aminocarbonylalkyl; aminoalkylcarbonylaminoalkyl; alkylcarbonylaminoalkyl; aminocarbonylalkylaminoalkyl; or alkoxycarbonylaminoalkyl.

In certain embodiments of formula I, formula IIa or formula IIb, m is 0 or 1, n is 1, and $R^2$ is:

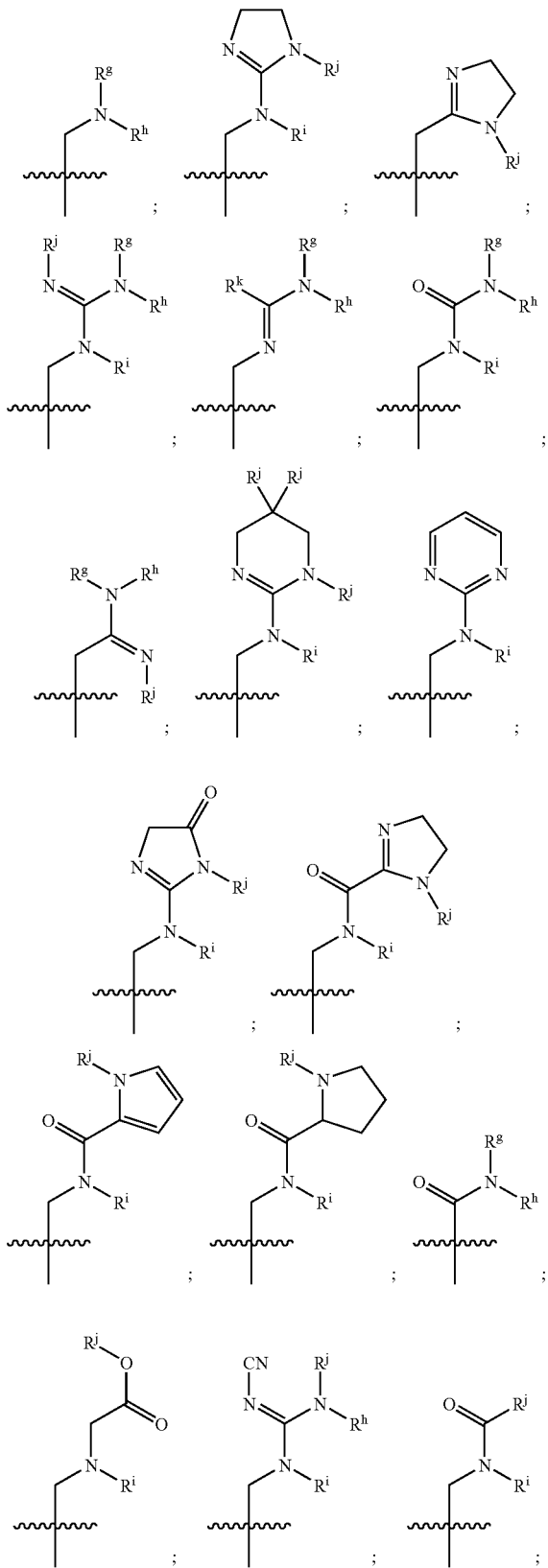

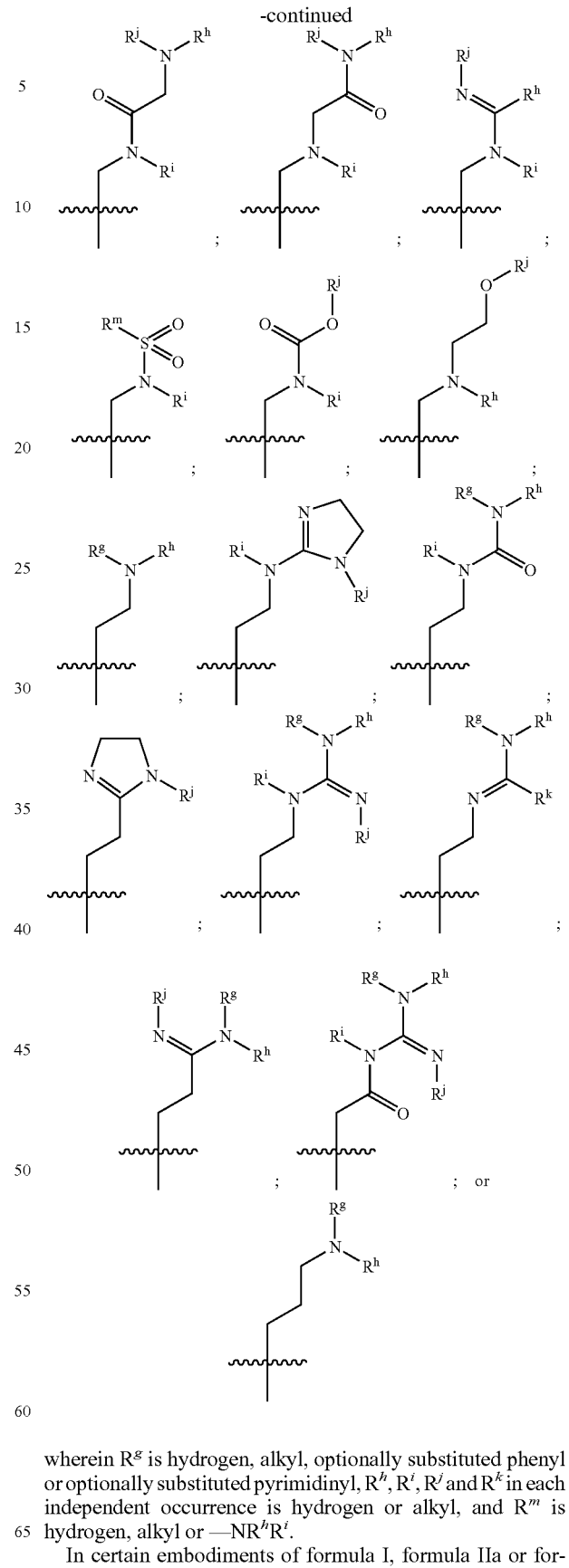

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, formula IIa or formula IIb, m is 0 or 1, n is 1, and $R^2$ is:

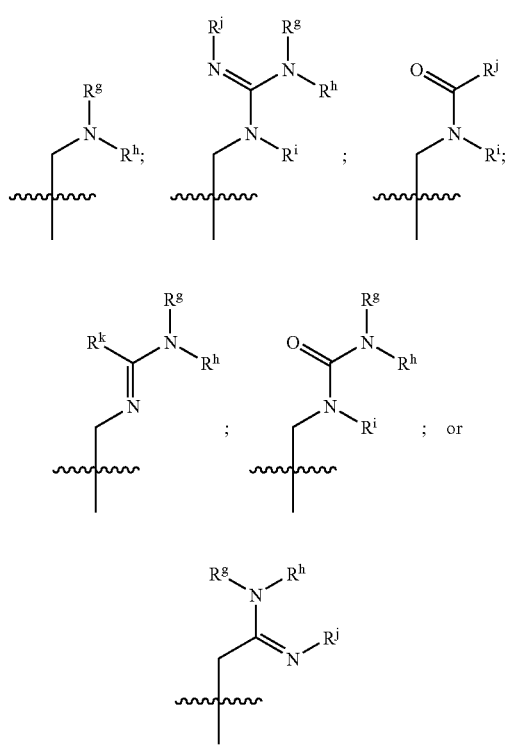

wherein $R^g$, $R^h$ and $R^i$ each independently is hydrogen or alkyl, and $R^j$ is hydrogen, alkyl or amino.

In certain embodiments of formula I, formula IIa or formula IIb, m is 0 or 1, n is 1, and $R^2$ is:

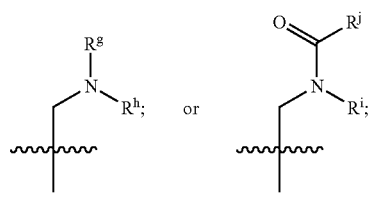

wherein $R^g$, $R^h$ and $R^i$ each independently is hydrogen or alkyl, and $R^j$ is hydrogen, alkyl or amino.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen or alkyl, and the other is:

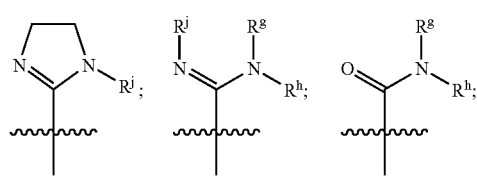

-continued

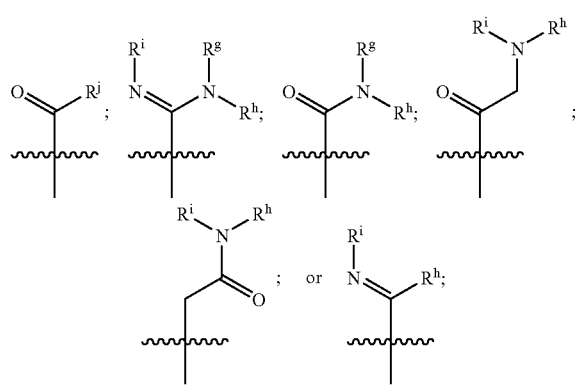

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —NR$^h$R$^i$.

In certain embodiments of formula I, formula IIa or formula IIb, m is 0 or 1, n is 1, Ar is optionally substituted phenyl, X is —SO$_2$—NH— or —NH—SO$_2$—, $R^3$ and $R^4$ are hydrogen, one of $R^5$ and $R^6$ is hydrogen or alkyl, and the other is:

wherein $R^g$, $R^h$ and $R^i$ each independently is hydrogen or alkyl, and $R^j$ is hydrogen, alkyl or amino.

In certain embodiments of formula I, formula IIa or formula IIb, m is 0 or 1, n is 1 or 2, and $R^3$ and $R^4$ together with the nitrogen to which they are attached form =NR$^f$ wherein $R^f$ is hydrogen, and wherein $R^5$ and $R^6$ are hydrogen.

In certain embodiments of formula I, formula IIa or formula IIb, m is 0 or 1, n is 1 or 2, and $R^3$ and $R^4$ together with the nitrogen to which they are attached form =O.

In certain embodiments of formula I, formula IIa or formula IIb, m is 0 or 1, and n is 2.

In certain embodiments of formula I, formula IIa or formula IIb, m is 0 or 1, n is 2, Ar is optionally substituted phenyl, X is —$SO_2$—NH— or —NH—$SO_2$—, and $R^3$ and $R^4$ are hydrogen.

In certain embodiments of formula I, formula IIa or formula IIb, m is 0 or 1, n is 2, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, formula IIa or formula IIb, m is 0 or 1, n is 2, Ar is optionally substituted phenyl, X is —$SO_2$—NH— or —NH—$SO_2$—, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, formula IIa or formula IIb, m is 0 or 1, n is 2, Ar is optionally substituted phenyl, X is —$SO_2$—NH— or —NH—$SO_2$—, $R^3$ and $R^4$ are hydrogen, one of $R^5$ and $R^6$ is hydrogen and the other is alkyl.

In certain embodiments of formula I, formula IIa or formula IIb, m is 0 or 1, n is 2, Ar is optionally substituted phenyl, X is —$SO_2$—NH— or —NH—$SO_2$—, $R^3$ and $R^4$ are hydrogen, one of $R^5$ and $R^6$ is hydrogen or alkyl, and the other is:

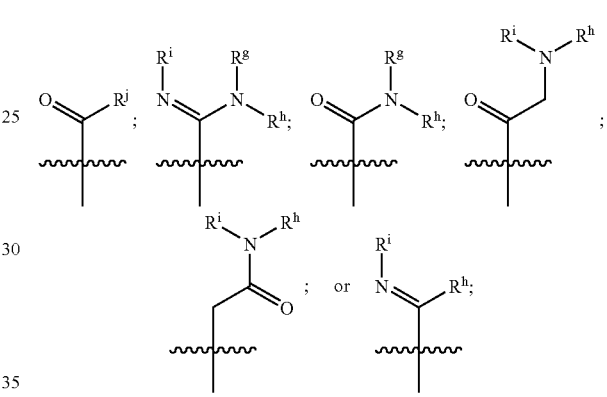

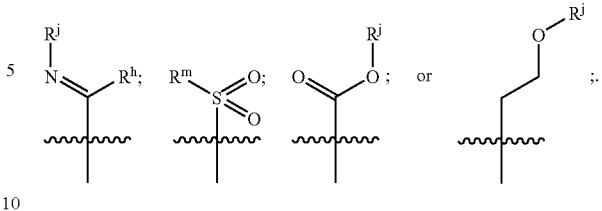

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, formula IIa or formula IIb, m is 0 or 1, n is 2, Ar is optionally substituted phenyl, X is —$SC_2$—NH— or —NH—$SO_2$—, $R^3$ and $R^4$ are hydrogen, one of $R^5$ and $R^6$ is hydrogen or alkyl, and the other is:

wherein $R^g$, $R^h$ and $R^i$ each independently is hydrogen or alkyl, and $R^j$ is hydrogen, alkyl or amino.

In certain embodiments of formula I, formula IIa or formula IIb, m is 0 or 1, and n is 3.

In certain embodiments of formula I, formula IIa or formula IIb, m is 0 or 1, n is 1, Ar is optionally substituted phenyl, X is —$SO_2$—NH— or —NH—$SO_2$—, and $R^3$ and $R^4$ are hydrogen.

In certain embodiments of formula I, formula IIa or formula IIb, m is 0 or 1, n is 3, Ar is optionally substituted phenyl, X is —$SO_2$—NH— or —NH—$SO_2$—, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula I, formula IIa or formula IIb, m is 0 or 1, n is 3, Ar is optionally substituted phenyl, X is —$SO_2$—NH— or —NH—$SO_2$—, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula I, formula IIa or formula IIb, m is 0 or 1, n is 3, Ar is optionally substituted phenyl, X is —$SO_2$—NH— or —NH—$SO_2$—, $R^3$ and $R^4$ are hydrogen, one of $R^5$ and $R^6$ is hydrogen or alkyl, and the other is:

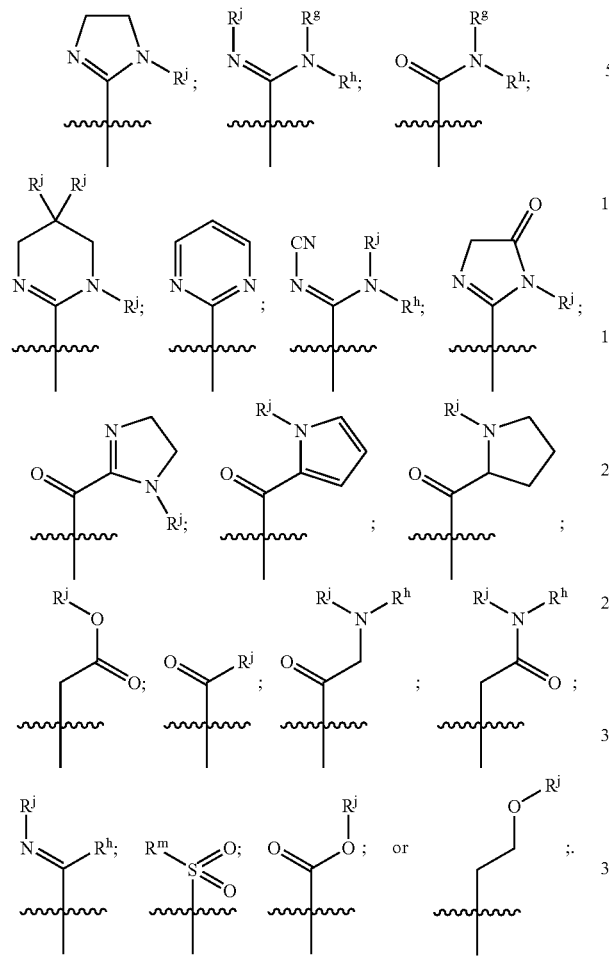

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula I, formula IIa or formula IIb, m is 0 or 1, n is 3, Ar is optionally substituted phenyl, X is —$SO_2$—NH— or —NH—$SO_2$—, $R^3$ and $R^4$ are hydrogen, one of $R^5$ and $R^6$ is hydrogen or alkyl, and the other is:

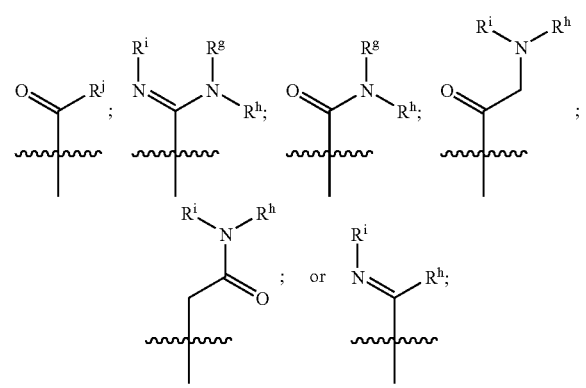

wherein $R^g$, $R^h$ and $R^i$ each independently is hydrogen or alkyl, and $R^j$ is hydrogen, alkyl or amino.

In certain embodiments of the invention, the subject compounds may be of the formula IIIa or IIIb:

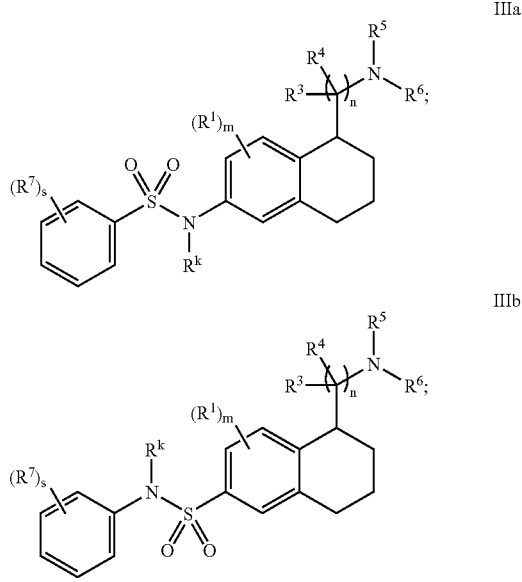

wherein:
s is from 0 to 4;
each $R^7$ is independently halo, alkyl, alkoxy, haloalkyl, heteroalkyl, cyano, —$S(O)_r$—$R^a$, —C(=O)—$NR^bR^c$, —$SO_2$—$NR^bR^c$, —$N(R^d)$—C(=O)—$R^e$, or —C(=O)—$R^e$, where r is from 0 to 2, $R^a$, $R^b$, $R^c$ and $R^d$ each independently is hydrogen or alkyl, and $R^e$ is hydrogen, alkyl, alkoxy or hydroxy; and
m, n, $R^1$, $R^3$, $R^4$, $R^5$ and $R^6$ are as defined herein.

In many embodiments of formula IIIa or formula IIIb, m is 0 or 1.

In certain embodiments of formula IIIa or formula IIIb, $R^1$ is halo.

In certain embodiments of formula IIIa or formula IIIb, m is 0 or 1 and $R^1$ is located at the 8-position of the tetralin ring system.

In certain embodiments of formula IIIa or formula IIIb, n is 1.

In certain embodiments of formula IIIa or formula IIIb, n is 2.

In certain embodiments of formula IIIa or formula IIIb, n is 3.

In many embodiments of formula IIIa or formula IIIb, s is 0 or 1.

In certain embodiments of formula IIIa or formula IIIb, $R^k$ is hydrogen.

In certain embodiments of formula IIIa or formula IIIb, $R^k$ is alkyl.

In certain embodiments of formula IIIa or formula IIIb, $R^k$ and one of $R^7$ form a $C_2$ or $C_3$ alkylene.

In many embodiments of formula IIIa or formula IIIb, m is 0 or 1 and $R^1$ is halo, preferably fluoro.

In many embodiments of formula IIIa or formula IIIb, s is 0 or 1 and $R^7$ is halo, preferably fluoro.

In certain embodiments of formula IIIa or formula IIIb, s is 0 or 1 and each $R^7$ is independently halo, alkyl, alkoxy or haloalkyl. Preferably $R^7$ is halo.

In certain embodiments of formula IIIa or formula IIIb, $R^3$ and $R^4$ are hydrogen.

In certain embodiments of formula IIIa or formula IIIb, one of $R^5$ and $R^6$ is hydrogen and the other is alkyl.

In certain embodiments of formula IIIa or formula IIIb, $R^5$ and $R^6$ are hydrogen.

In certain embodiments of formula IIIa or formula IIIb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula IIIa or formula IIIb, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IIIa or formula IIIb, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IIIa or formula IIIb, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula IIIa or formula IIIb, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of formula IIIa or formula IIIb, $R^5$ and $R^6$ together with the nitrogen to which they are attached form an amidinyl group.

In certain embodiments of formula IIIa or formula IIIb, $R^5$ and $R^6$ together with the nitrogen to which they are attached form a guanidinyl group.

In certain embodiments of formula IIIa or formula IIIb, $R^5$ and $R^6$ together with the nitrogen to which they are attached form a urea group.

In certain embodiments of formula IIIa or formula IIIb, $R^3$ and $R^4$ together with the nitrogen to which they are attached form $=NR^f$ wherein $R^f$ is hydrogen.

In certain embodiments of formula IIIa or formula IIIb, $R^3$ and $R^4$ together with the nitrogen to which they are attached form $=O$.

In certain embodiments of formula IIIa or formula IIIb, one of $R^5$ and $R^6$ and one of $R^3$ and $R^4$ together with the atoms to which they are attached form an imidazolinyl ring.

In certain embodiments of formula IIIa or formula IIIb, $R^5$ and $R^6$ together with the nitrogen to which they are attached form or a five- or six-membered heteroaryl ring that is optionally substituted and which optionally includes an additional nitrogen heteroatom.

In certain embodiments of formula IIIa or formula IIIb, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula IIIa or formula IIIb, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula IIIa or formula IIIb, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula IIIa or formula IIIb, one of $R^5$ and $R^6$ and one of $R^3$ and $R^4$ together with the atoms to which they are attached form an imidazolinyl ring.

In certain embodiments of formula IIIa or formula IIIb, s is from 0 to 2 and $R^7$ is halo, alkyl, alkoxy, haloalkyl, hydroxy, cyano or methanesulfonyl.

In certain embodiments of formula IIIa or formula IIIb, s is 0 or 1 and $R^7$ is halo.

In certain embodiments of formula IIIa or formula IIIb, m is 0 or 1, and n is 1.

In certain embodiments of formula IIIa or formula IIIb, m is 0 or 1, is 1 and $R^k$ is hydrogen.

In certain embodiments of formula IIIa or formula IIIb, m is 0 or 1, n is 1, $R^k$ is hydrogen and $R^3$ and $R^4$ are hydrogen.

In certain embodiments of formula IIIa or formula IIIb, m is 0 or 1, n is 1, $R^k$ is hydrogen, s is 0 or 1, $R^1$ and $R^7$ are halo, $R^3$ and $R^4$ are hydrogen, one of $R^5$ and $R^6$ is hydrogen, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IIIa or formula IIIb, m is 0 or 1, n is 1, $R^k$ is hydrogen, s is 0 or 1, $R^1$ and $R^7$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IIIa or formula IIIb, m is 0 or 1, n is 1, $R^k$ is hydrogen, s is 0 or 1, $R^1$ and $R^7$ are halo, $R^3$ and $R^4$ are hydrogen, one of $R^5$ and $R^6$ is hydrogen and the other is alkyl.

In certain embodiments of formula IIIa or formula IIIb, m is 0 or 1, n is 1, $R^k$ and one of $R^7$ form a $C_2$ or $C_3$ alkylene, s is 0, 1 or 2, $R^1$ and $R^7$ are halo, $R^3$ and $R^4$ are hydrogen, one of $R^5$ and $R^6$ is hydrogen and the other is alkyl.

In certain embodiments of formula IIIa or formula IIIb, m is 0 or 1, n is 1, $R^k$ is hydrogen, s is 0 or 1, $R^1$ and $R^7$ are halo, $R^3$ and $R^4$ are hydrogen, one of $R^5$ and $R^6$ is hydrogen, and the other is:

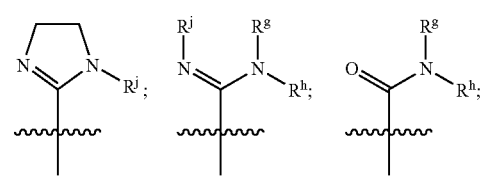

-continued

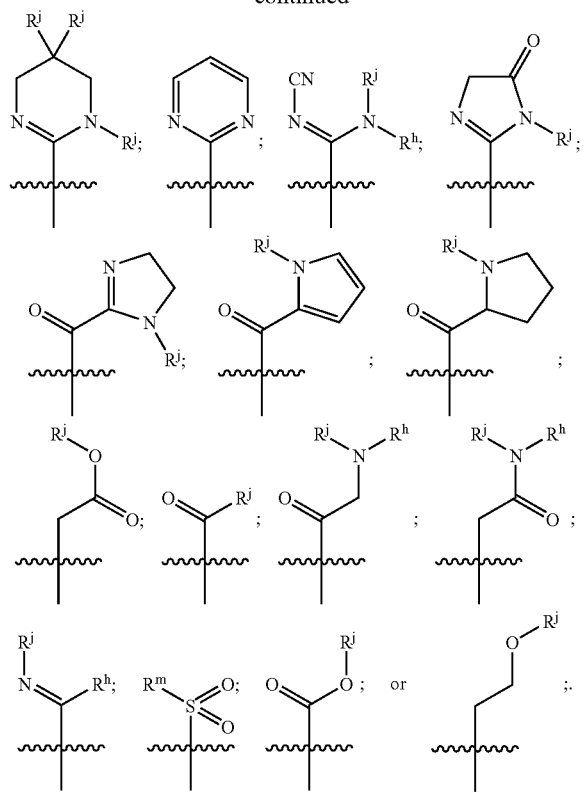

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula IIIa or formula IIIb, m is 0 or 1, n is 1, $R^k$ is hydrogen, s is 0 or 1, $R^1$ and $R^7$ are halo, $R^3$ and $R^4$ are hydrogen, one of $R^5$ and $R^6$ is hydrogen, and the other is:

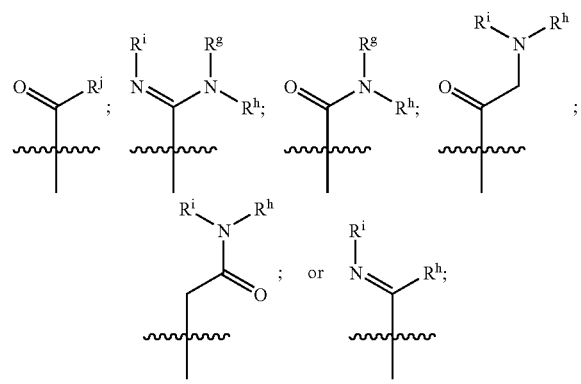

wherein $R^g$, $R^h$ and $R^i$ each independently is hydrogen or alkyl, and $R^j$ is hydrogen, alkyl or amino.

In certain embodiments of formula IIIa or formula IIIb, m is 0 or 1, $R^k$ is hydrogen, n is 1, $R^3$ and $R^4$ are hydrogen, one of $R^5$ and $R^6$ is hydrogen and the other is: hydrogen; alkyl; alkylcarbonyl; or aminocarbonyl.

In certain embodiments of formula IIIa or formula IIIb, m is 0 or 1, $R^k$ is hydrogen, n is 1, $R^3$ and $R^4$ are hydrogen, one of $R^5$ and $R^6$ is hydrogen and the other is alkyl.

In certain embodiments of formula IIIa or formula IIIb, m is 0 or 1, n is 1, $R^k$ is hydrogen, $R^3$ and $R^4$ are hydrogen, one of $R^5$ and $R^6$ is hydrogen and the other is alkylcarbonyl.

In certain embodiments of formula I, formula IIIa or formula IIIb, m is 0 or 1, $R^k$ is hydrogen, n is 1, $R^3$ and $R^4$ are hydrogen, one of $R^5$ and $R^6$ is hydrogen and the other is aminocarbonyl.

In certain embodiments of formula IIIa or formula IIIb, m is 0 or 1, n is 1 or 2, $R^k$ is hydrogen, s is 0 or 1, $R^1$ and $R^7$ are halo, and $R^3$ and $R^4$ together with the nitrogen to which they are attached form =$NR^f$ wherein $R^f$ is hydrogen, and wherein $R^5$ and $R^6$ are hydrogen.

In certain embodiments of formula IIIa or formula IIIb, m is 0 or 1, n is 1 or 2, $R^k$ is hydrogen, s is 0 or 1, $R^1$ and $R^8$ are halo, and $R^3$ and $R^4$ together with the nitrogen to which they are attached form =O.

In certain embodiments of formula IIIa or formula IIIb, m is 0 or 1, and n is 2.

In certain embodiments of formula IIIa or formula IIIb, m is 0 or 1, n is 2, $R^k$ is hydrogen, and $R^3$ and $R^4$ are hydrogen.

In certain embodiments of formula IIIa or formula IIIb, m is 0 or 1, n is 2, $R^k$ is hydrogen, $R^k$ is hydrogen, s is 0 or 1, $R^1$ and $R^7$ are halo, $R^3$ and $R^4$ are hydrogen, one of $R^5$ and $R^6$ is hydrogen, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IIIa or formula IIIb, m is 0 or 1, n is 2, $R^k$ is hydrogen, s is 0 or 1, $R^1$ and $R^7$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IIIa or formula IIIb, m is 0 or 1, n is 2, $R^k$ is hydrogen, s is 0 or 1, $R^1$ and $R^8$ are halo, $R^3$ and $R^4$ are hydrogen, one of $R^5$ and $R^6$ is hydrogen and the other is alkyl.

In certain embodiments of formula IIIa or formula IIIb, m is 0 or 1, n is 2, $R^k$ is hydrogen, s is 0 or 1, $R^1$ and $R^8$ are halo, $R^3$ and $R^4$ are hydrogen, one of $R^5$ and $R^6$ is hydrogen or alkyl, and the other is:

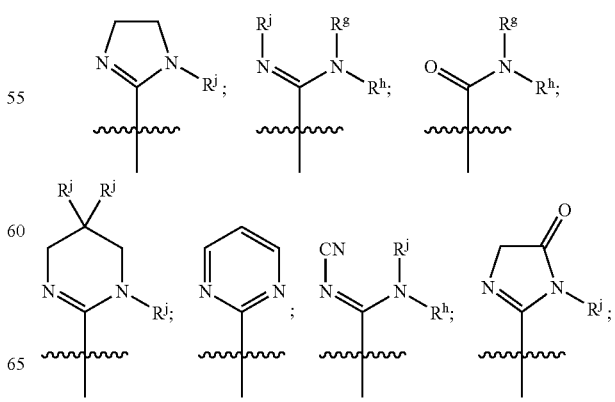

-continued

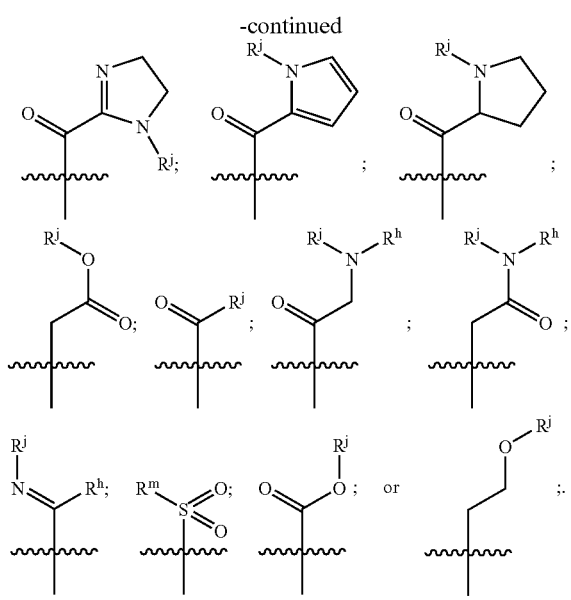

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula IIIa or formula IIIb, m is 0 or 1, n is 2, $R^k$ is hydrogen, s is 0 or 1, $R^1$ and $R^8$ are halo, $R^3$ and $R^4$ are hydrogen, one of $R^5$ and $R^6$ is hydrogen or alkyl, and the other is:

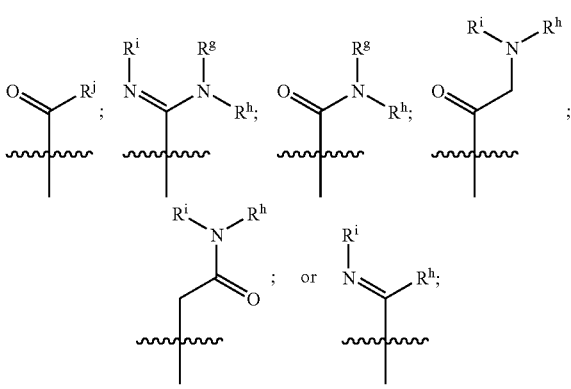

wherein $R^g$, $R^h$ and $R^i$ each independently is hydrogen or alkyl, and $R^j$ is hydrogen, alkyl or amino.

In certain embodiments of formula IIIa or formula IIIb, m is 0 or 1, and n is 3.

In certain embodiments of formula IIIa or formula IIIb, m is 0 or 1, n is 1, and $R^3$ and $R^4$ are hydrogen.

In certain embodiments of formula IIIa or formula IIIb, m is 0 or 1, n is 3, $R^k$ is hydrogen, s is 0 or 1, $R^1$ and $R^8$ are halo, $R^3$ and $R^4$ are hydrogen, one of $R^5$ and $R^6$ is hydrogen or alkyl, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IIIa or formula IIIb, m is 0 or 1, n is 3, $R^k$ is hydrogen, s is 0 or 1, $R^1$ and $R^8$ are halo, $R^3$ and $R^4$ are hydrogen, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IIIa or formula IIIb, m is 0 or 1, n is 3, s is 0 or 1, $R^1$ and $R^8$ are halo, $R^3$ and $R^4$ are hydrogen, one of $R^5$ and $R^6$ is hydrogen or alkyl, and the other is:

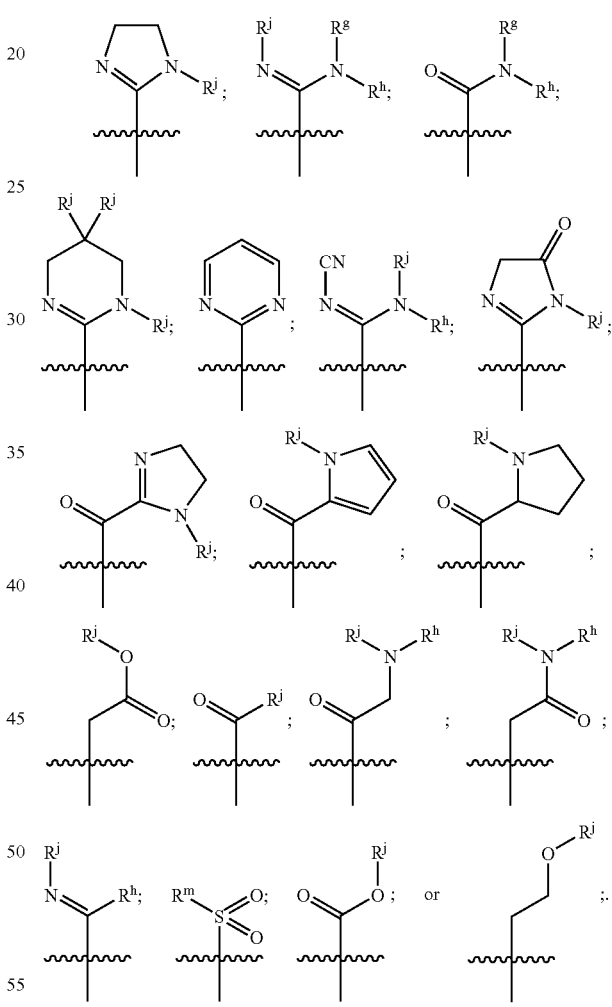

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or —$NR^hR^i$.

In certain embodiments of formula IIIa or formula IIIb, m is 0 or 1, n is 3, $R^k$ is hydrogen, s is 0 or 1, $R^1$ and $R^8$ are halo, $R^3$ and $R^4$ are hydrogen, one of $R^5$ and $R^6$ is hydrogen or alkyl, and the other is:

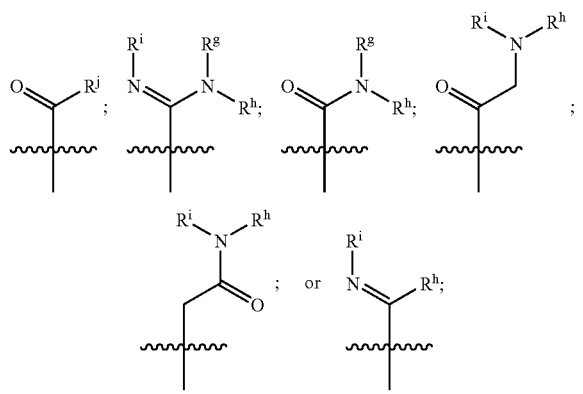

wherein $R^g$, $R^h$ and $R^i$ each independently is hydrogen or alkyl, and $R^j$ is hydrogen, alkyl or amino.

The subject compounds may, in certain embodiments, be more specifically of formula IVa, IVb, IVc or IVd:

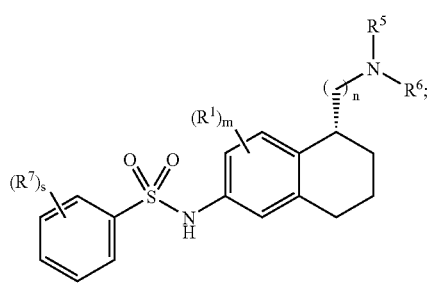

IVa

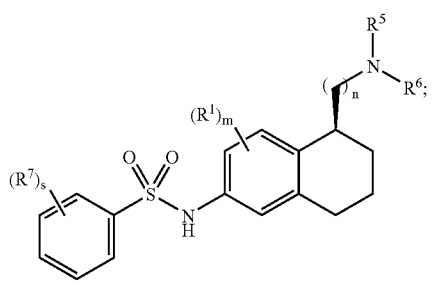

IVb

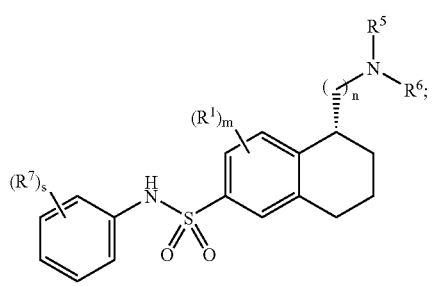

IVc

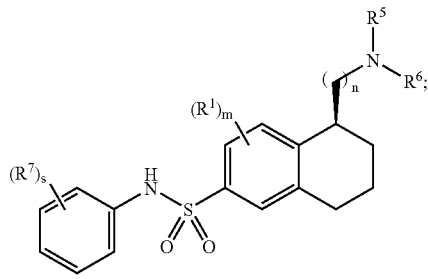

IVd wherein m, n, s, $R^1$, $R^5$, $R^6$ and $R^7$ are as defined herein.

In many embodiments of formula IVa, formula IVb, formula IVc or formula IVd, m is 0 or 1.

In certain embodiments of formula IVa, formula IVb, formula IVc or formula IVd, $R^1$ is halo.

In certain embodiments of formula IVa, formula IVb, formula IVc or formula IVd, m is 0 or 1 and $R^1$ is located at the 8-position of the tetralin ring system.

In certain embodiments of formula IVa, formula IVb, formula IVc or formula IVd, n is 1.

In certain embodiments of formula IVa, formula IVb, formula IVc or formula IVd, n is 2.

In certain embodiments of formula IVa, formula IVb, formula IVc or formula IVd, n is 3.

In certain embodiments of formula IVa, formula IVb, formula IVc or formula IVd, one of $R^5$ and $R^6$ is hydrogen and the other is alkyl.

In certain embodiments of formula IVa, formula IVb, formula IVc or formula IVd, $R^5$ and $R^6$ are hydrogen.

In certain embodiments of formula IVa, formula IVb, formula IVc or formula IVd, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; or alkoxalkyl.

In certain embodiments of formula IVa, formula IVb, formula IVc or formula IVd, one of $R^5$ and $R^6$ is hydrogen or alkyl and the other is: hydrogen; methyl; acetyl; or aminocarbonyl.

In certain embodiments of formula IVa, formula IVb, formula IVc or formula IVd, s is 0 or 1 and each $R^7$ is independently halo, alkyl, alkoxy or haloalkyl. Preferably $R^7$ is halo.

In certain embodiments of formula IVa, formula IVb, formula IVc or formula IVd, one of $R^5$ and $R^6$ is hydrogen or alkyl and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IVa, formula IVb, formula IVc or formula IVd, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IVa, formula IVb, formula IVc or formula IVd, one of $R^5$ and $R^6$ is hydrogen and the other is heteroaryl selected from benzothiazolyl, indolyl, thienyl, furanyl, pyridinyl, pyrimdinyl, pyrrolyl, pyrazolyl and imidazolyl, each optionally substituted.

In certain embodiments of formula IVa, formula IVb, formula IVc or formula IVd, one of $R^5$ and $R^6$ is hydrogen and the other is heteroaryl selected from pyrimidinyl, benzothiazol-2-yl, and 5,5-dimethyl-1,4,5,6-tetrahydropyrimidinyl.

In certain embodiments of formula IVa, formula IVb, formula IVc or formula IVd, $R^5$ and $R^6$ together with the nitrogen to which they are attached form an amidinyl group.

In certain embodiments of formula IVa, formula IVb, formula IVc or formula IVd, $R^5$ and $R^6$ together with the nitrogen to which they are attached form a guanidinyl group.

In certain embodiments of formula IVa, formula IVb, formula IVc or formula IVd, $R^5$ and $R^6$ together with the nitrogen to which they are attached form a urea group.

In certain embodiments of formula IVa, formula IVb, formula IVc or formula IVd, $R^5$ and $R^6$ together with the nitrogen to which they are attached form or a five- or six-membered heteroaryl ring that is optionally substituted and which optionally includes an additional nitrogen heteroatom.

In certain embodiments of formula IVa, formula IVb, formula IVc or formula IVd, $R^5$ and $R^6$ together with the nitrogen to which they are attached form or a five- or six-membered heteroaryl ring selected from pyridinyl, pyrimidinyl, pyrrolyl, imidazolyl or pyrazolyl, each optionally substituted.

In certain embodiments of formula IVa, formula IVb, formula IVc or formula IVd, $R^5$ and $R^6$ together with the nitrogen to which they are attached form they are attached form or a five- or six-membered heterocyclic ring that is optionally substituted and which optionally includes an additional heteroatom selected from O, N and S.

In certain embodiments of formula IVa, formula IVb, formula IVc or formula IVd, $R^5$ and $R^6$ together with the nitrogen to which they are attached form they are attached form or a five- or six-membered heterocyclic ring selected from pyrrolidinyl, piperidinyl, piperazinyl, morpholinyl, azepinyl and diazepinyl.

In certain embodiments of formula IVa, formula IVb, formula IVc or formula IVd, one of $R^5$ and $R^6$ and one of $R^3$ and $R^4$ together with the atoms to which they are attached form an imidazolinyl ring.

In certain embodiments of formula IVa, formula IVb, formula IVc or formula IVd, s is from 0 to 2 and $R^7$ is halo, alkyl, alkoxy, haloalkyl, hydroxy, cyano or methanesulfonyl.

In certain embodiments of formula IVa, formula IVb, formula IVc or formula IVd, s is 0 or 1 and $R^7$ is halo.

In certain embodiments of formula IVa, formula IVb, formula IVc or formula IVd, m is 0 or 1, and n is 1.

In certain embodiments of formula IVa, formula IVb, formula IVc or formula IVd, m is 0 or 1, n is 1, s is 0 or 1, $R^1$ and $R^7$ are halo, one of $R^5$ and $R^6$ is hydrogen, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IVa, formula IVb, formula IVc or formula IVd, m is 0 or 1, n is 1, s is 0 or 1, $R^1$ and $R^7$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IVa, formula IVb, formula IVc or formula IVd, m is 0 or 1, n is 1, s is 0 or 1, $R^1$ and $R^7$ are halo, one of $R^5$ and $R^6$ is hydrogen and the other is alkyl.

In certain embodiments of formula IVa, formula IVb, formula IVc or formula IVd, m is 0 or 1, n is 1, s is 0 or 1, $R^1$ and $R^8$ are halo, one of $R^5$ and $R^6$ is hydrogen, and the other is:

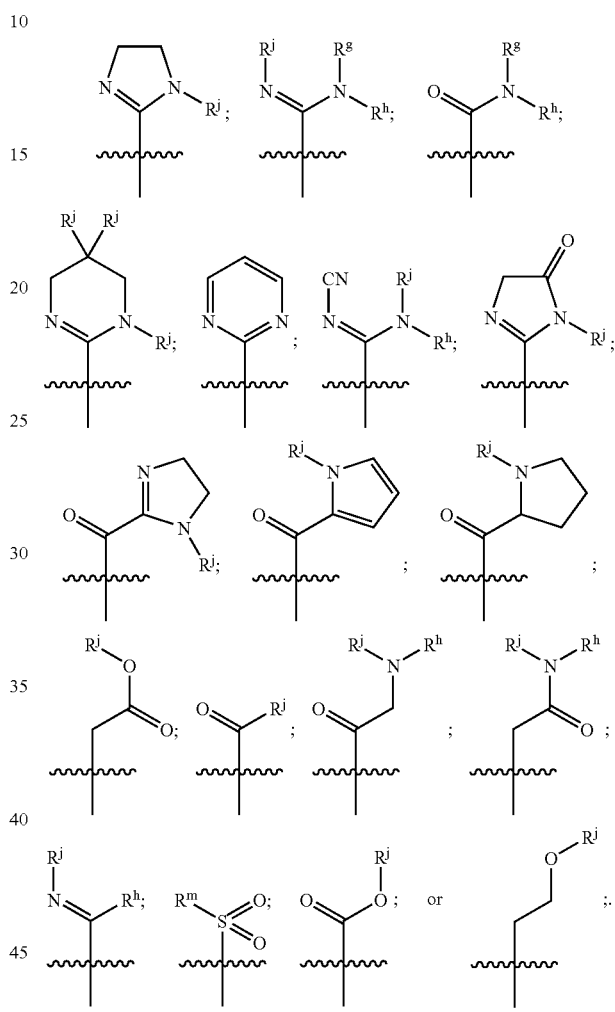

wherein $R^g$ is hydrogen, alkyl, optionally substituted phenyl or optionally substituted pyrimidinyl, $R^h$, $R^i$, $R^j$ and $R^k$ in each independent occurrence is hydrogen or alkyl, and $R^m$ is hydrogen, alkyl or $-NR^hR^i$.

In certain embodiments of formula IVa, formula IVb, formula IVc or formula IVd, m is 0 or 1, n is 1, s is 0 or 1, $R^1$ and $R^7$ are halo, one of $R^5$ and $R^6$ is hydrogen, and the other is:

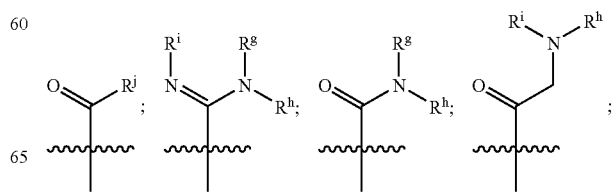

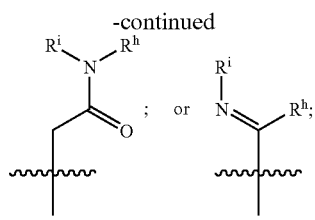

wherein $R^g$, $R^h$ and $R^i$ each independently is hydrogen or alkyl, and $R^j$ is hydrogen, alkyl or amino.

In certain embodiments of formula IVa, formula IVb, formula IVc or formula IVd, m is 0 or 1, and n is 2.

In certain embodiments of either of formula IIIa or IIIb, m is 0 or 1, n is 2, s is 0 or 1, $R^1$ and $R^8$ are halo, one of $R^5$ and $R^6$ is hydrogen, and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen and the other is: hydrogen; alkyl; aminocarbonyl; or alkylcarbonyl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen and the other is alkyl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen and the other is alkylcarbonyl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen and the other is aminocarbonyl.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen, and the other is:

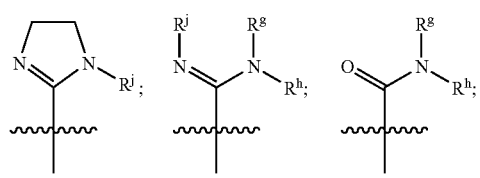

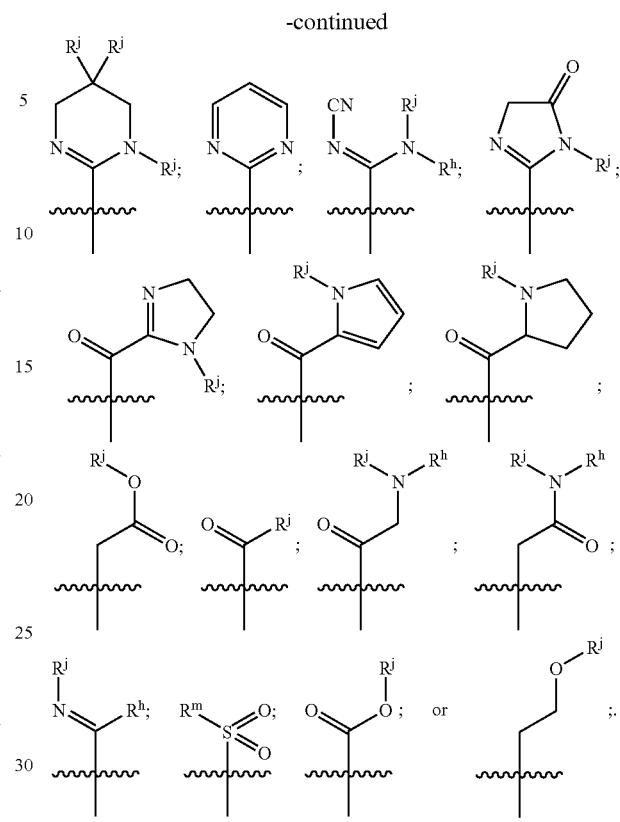

wherein $R^g$ is hydrogen, alkyl, optionally substituted phenyl or optionally substituted pyrimidinyl, $R^h$, $R^i$, $R^j$ and $R^k$ in each independent occurrence is hydrogen, and $R^m$ is hydrogen, alkyl or —$NR^hR^i$.

In certain embodiments of formula IVa, formula IVb, formula IVc or formula IVd, m is 0 or 1, n is 2, s is 0 or 1, $R^1$ and $R^8$ are halo, one of $R^5$ and $R^6$ is hydrogen, and the other is:

wherein $R^g$, $R^h$ and $R^i$ each independently is hydrogen or alkyl, and $R^j$ is hydrogen, alkyl or amino.

In certain embodiments of formula IVa, formula IVb, formula IVc or formula IVd, m is 0 or 1, and n is 3.

In certain embodiments of formula IVa, formula IVb, formula IVc or formula IVd, m is 0 or 1, n is 3, s is 0 or 1, $R^1$ and $R^8$ are halo, one of $R^5$ and $R^6$ is hydrogen, and the other is: hydrogen; alkyl; amidinyl; aminocarbonyl; alkylcarbonyl;

alkoxycarbonyl; aminocarbonylalkyl; aminoalkylcarbonyl; alkoxycarbonylalkyl; imidazolonyl; imidazolylcarbonyl; pyrrolylcarbonyl; pyrrolidinylcarbonyl; N-cyanoamidinyl; alkylsulfonyl; hydroxyalkylcarbonyl; aminosulfonyl; hydroxyalkyl; alkoxalkyl; or optionally substituted heteroaryl.

In certain embodiments of formula IVa, formula IVb, formula IVc or formula IVd, m is 0 or 1, n is 3, s is 0 or 1, $R^1$ and $R^8$ are halo, one of $R^5$ and $R^6$ is hydrogen and the other is: hydrogen; alkyl; amidinyl; aminocarbonyl; alkylcarbonyl; alkoxycarbonyl; aminocarbonylalkyl; aminoalkylcarbonyl; alkoxycarbonylalkyl; alkylsulfonyl; or hydroxyalkylcarbonyl.

In certain embodiments of formula IVa, formula IVb, formula IVc or formula IVd, m is 0 or 1, n is 3, s is 0 or 1, $R^1$ and $R^8$ are halo, one of $R^5$ and $R^6$ is hydrogen, and the other is:

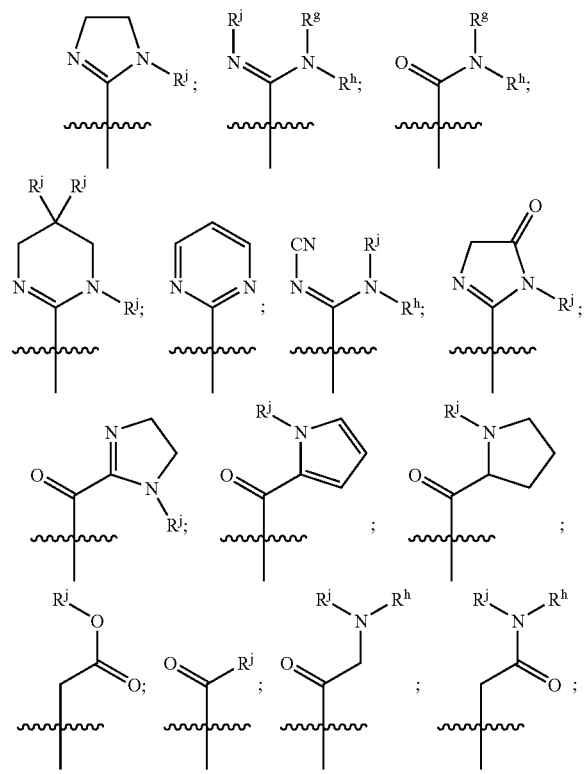

-continued

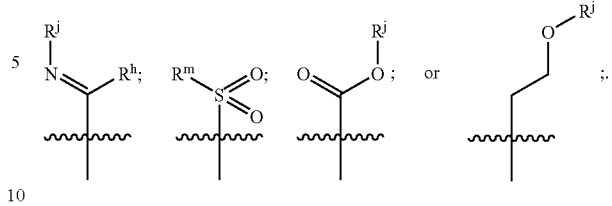

wherein $R^g$ is hydrogen, alkyl, optionally substituted phenyl or optionally substituted pyrimidinyl, $R^h$, $R^i$, $R^j$ and $R^k$ in each independent occurrence is hydrogen, and $R^m$ is hydrogen, alkyl or $-NR^hR^i$.

In certain embodiments of formula IVa, formula IVb, formula IVc or formula IVd, m is 0 or 1, n is 3, s is 0 or 1, $R^1$ and $R^8$ are halo, one of $R^5$ and $R^6$ is hydrogen, and the other is:

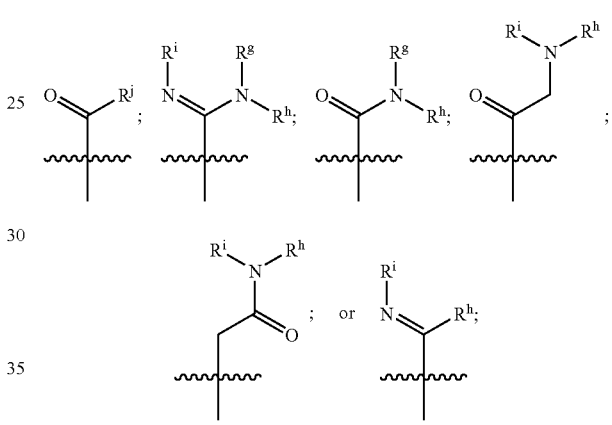

wherein $R^g$, $R^h$ and $R^i$ each independently is hydrogen or alkyl, and $R^j$ is hydrogen, alkyl or amino.

Where any of $R^1$, $R^2$, $R^3$, $R^4$, $R^5$, $R^6$, $R^7$, $R^8$, $R^a$, $R^b$, $R^c$, $R^d$, $R^e$, $R^f$, $R^g$, $R^h$, $R^i$, $R^j$, $R^k$ and $R^m$ herein are alkyl or contain an alkyl moiety, such alkyl is preferably lower alkyl, i.e. $C_1$-$C_6$alkyl, and more preferably $C_1$-$C_4$alkyl.

Representative compounds in accordance with the invention are shown in Table 1.

TABLE 1

| # | Structure | Name (Autonom ™) | Mp ° C. or M + H |
|---|---|---|---|
| 1 | 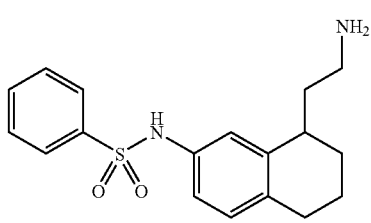 | N-[8-(2-Amino-ethyl)-5,6,7,8-tetrahydro-naphthalen-2-yl]-benzenesulfonamide | 160.5-165° C. HCl salt |

TABLE 1-continued

| # | Structure | Name (Autonom ™) | Mp ° C. or M + H |
|---|---|---|---|
| 2 | 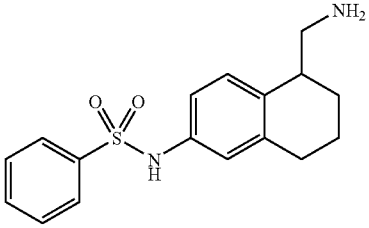 | N-(5-Aminomethyl-5,6,7,8-tetrahydro-naphthalen-2-yl)-benzenesulfonamide | 317 |
| 3 | 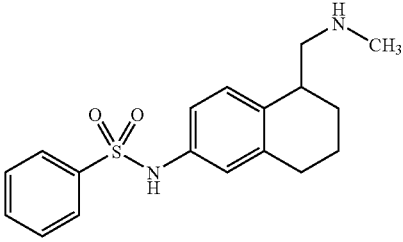 | N-(5-Methylaminomethyl-5,6,7,8-tetrahydro-naphthalen-2-yl)-benzenesulfonamide | 331 |
| 4 | 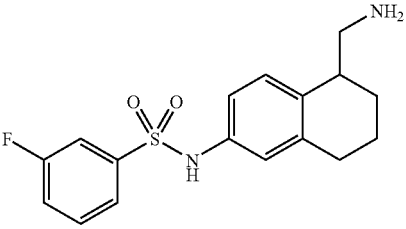 | N-(5-Aminomethyl-5,6,7,8-tetrahydro-naphthalen-2-yl)-3-fluoro-benzenesulfonamide | 335 |
| 5 | 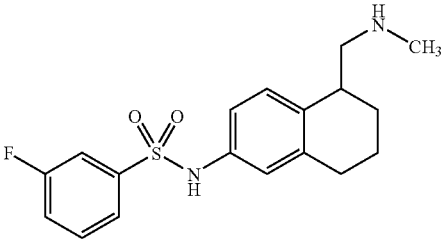 | 3-Fluoro-N-(5-methylaminomethyl-5,6,7,8-tetrahydro-naphthalen-2-yl)-benzenesulfonamide | 349 |
| 6 | 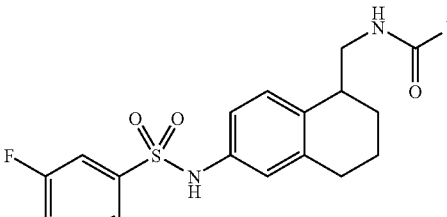 | 3-Fluoro-N-(5-ureidomethyl-5,6,7,8-tetrahydro-naphthalen-2-yl)-benzenesulfonamide | 378 |
| 7 | 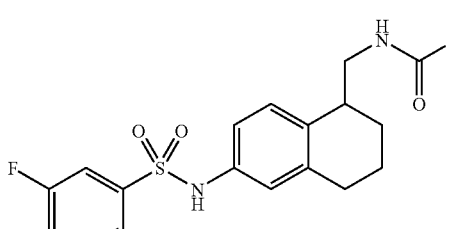 | 3-Fluoro-N-(5-formylaminomethyl-5,6,7,8-tetrahydro-naphthalen-2-yl)-benzenesulfonamide | 363 |

TABLE 1-continued

| # | Structure | Name (Autonom ™) | Mp ° C. or M + H |
|---|---|---|---|
| 8 | 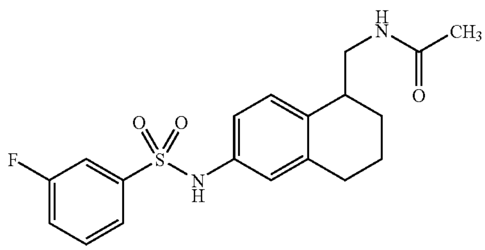 | N-[6-(3-Fluoro-benzenesulfonylamino)-1,2,3,4-tetrahydro-naphthalen-1-ylmethyl]-acetamide | 377 |
| 9 | 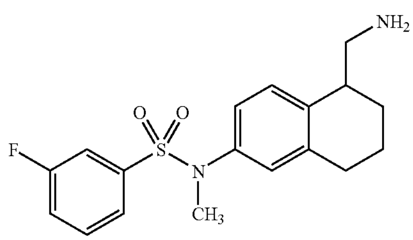 | N-(5-Aminomethyl-5,6,7,8-tetrahydro-naphthalen-2-yl)-3-fluoro-N-methyl-benzenesulfonamide | 349 |
| 10 | 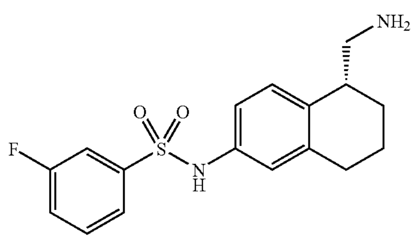 | (S)-N-(5-Aminomethyl-5,6,7,8-tetrahydro-naphthalen-2-yl)-3-fluoro-benzenesulfonamide | 142-144° C. |
| 11 | 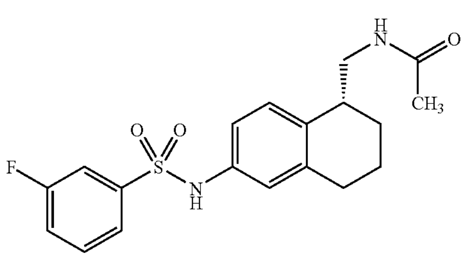 | (S)-N-[6-(3-Fluoro-benzenesulfonylamino)-1,2,3,4-tetrahydro-naphthalen-1-ylmethyl]-acetamide | 377 |
| 12 | 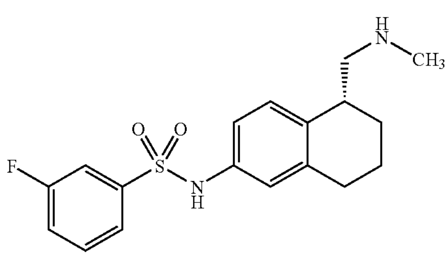 | (S)-3-Fluoro-N-(5-methylaminomethyl-5,6,7,8-tetrahydro-naphthalen-2-yl)-benzenesulfonamide | 349 |
| 13 | 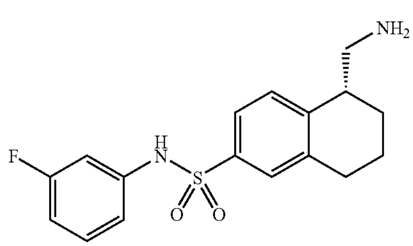 | 5-Aminomethyl-5,6,7,8-tetrahydro-naphthalene-2-sulfonic acid (3-fluoro-phenyl)-amide | 335 |

TABLE 1-continued

| # | Structure | Name (Autonom ™) | Mp ° C. or M + H |
|---|---|---|---|
| 14 | 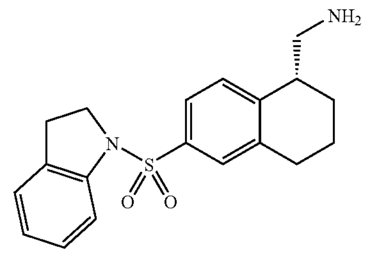 | C-[6-(2,3-Dihydro-indole-1-sulfonyl)-1,2,3,4-tetrahydro-naphthalen-1-yl]-methylamine | 146-147° C. |
| 15 | 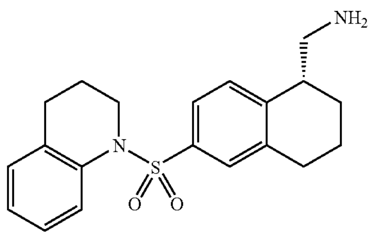 | C-[6-(3,4-Dihydro-2H-quinoline-1-sulfonyl)-1,2,3,4-tetrahydro-naphthalen-1-yl]-methylamine | 130-131° C. |

Another aspect of the invention provides a composition comprising a therapeutically effective amount of at least one compound of formula (I) and a pharmaceutically acceptable carrier.

Yet another aspect of the invention provides a method for treating a central nervous system (CNS) disease state in a subject comprising administering to the subject a therapeutically effective amount of a compound of formula I. The disease state may comprise, for example, psychoses, schizophrenia, manic depressions, neurological disorders, memory disorders, attention deficit disorder, Parkinson's disease, amyotrophic lateral sclerosis, Alzheimer's disease or Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 2004, Volumes 1-56. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein Ar, m, X and $R^1$ are as defined herein. Numerous synthetic routes to indane and tetralin compounds are known and may be used in preparation of the subject compounds, and the procedure of Scheme A is only exemplary. Specific examples of the procedure of Scheme A are provided in the following Experimental section.

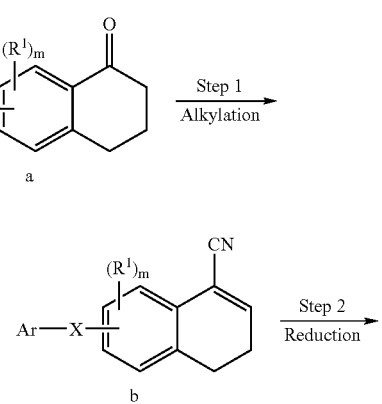

SCHEME A

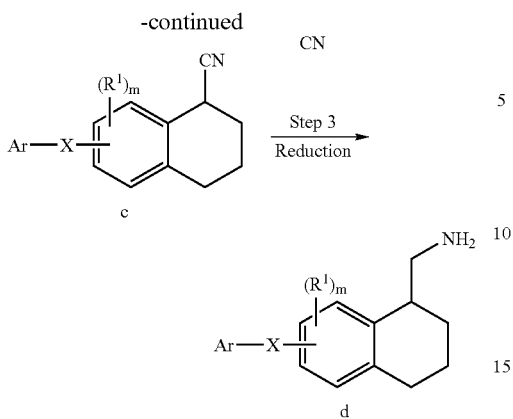

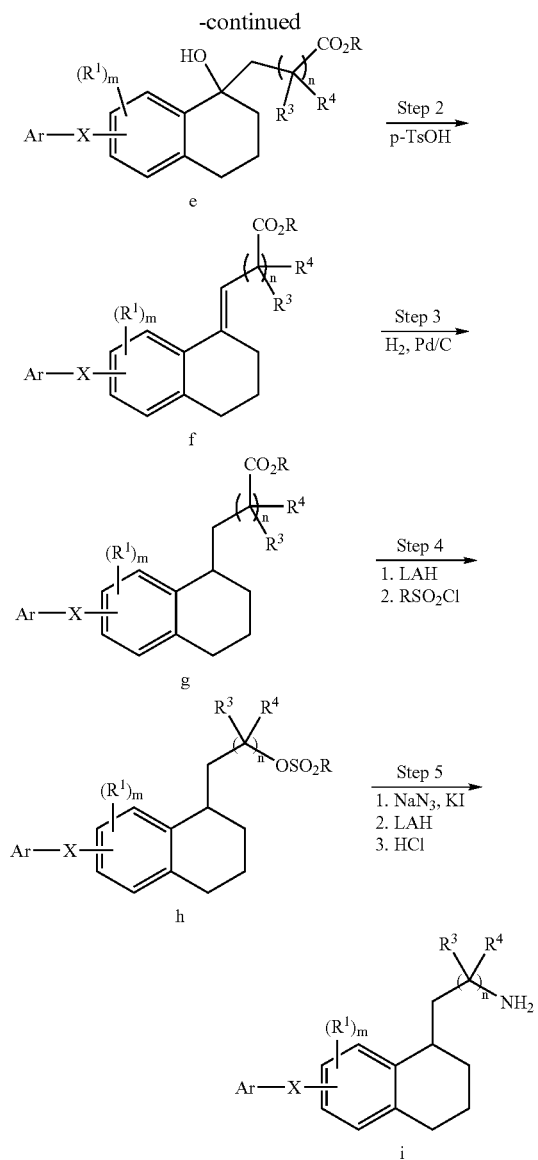

In step 1 of Scheme A, ketone compound a undergoes an alkylation/cyanylation reaction to give an arylsulfonyl nitrile compound b. Ketone compound may comprise, for example, an arylsulfonamidyl tetralone or an arylaminosulfonyl tetralone. Ketone compounds a may be prepared by a variety of techniques known in the art. The alkylation reaction of step 1 may be achieved by treatment of ketone compound a with trimethylsilyl cyanide in the presence of zinc iodide under polar aprotic solvent conditions, followed by treatment with p-toluene sulfonic acid or like acid.

In step 2, nitrile compound b is subject to ring atom reduction to provide nitrile compound c. This reduction removes a residual unsaturation resulting from step 1, and may be carried out using hydrogen gas with a platinum or palladium catalyst.

A second reduction reaction is carried out in step 3 to reduce the nitrile group of compound c and afford an aminomethyl compound d. Compound d is a compound of formula I in accordance with the invention.

Many variations on the procedure of Scheme A are possible and will be readily apparent to those skilled in the art. In certain embodiments the reduction reactions of step 2 and step 3 may be performed in a single step. In other embodiments, the reduction of step 2 may be omitted to provide an additional unsaturation. The amine compound d may be subject to additional alkylation reaction, using suitable protection/deprotection to afford monoalkylamino or dialkylamino compounds. Amine compound d may also undergo subsequent reaction to form amidinyl, guanidinyl, imidazolinyl, imidazolinylamino, and other functionalities. Specific examples of such additional reactions are provided in the Examples below.

Referring to Scheme B, another synthetic route for the subject compounds is shown, wherein Y is a leaving group and may be the same or different in each occurrence, R is lower alkyl and may be the same or different in each occurrence, and Ar, m, X, $R^1$, $R^3$ and $R^4$ are as defined herein.

SCHEME B

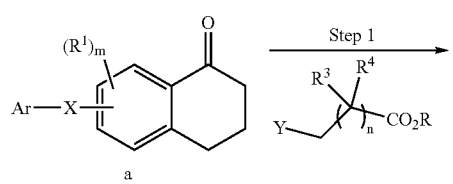

In step 1 of Scheme B, ketone compound a is subject to an alkylation reaction to afford a hydroxy ester compound e. Alkylation in step 1 may be effected by treatment of ketone compound a with zinc and iodine, followed by a haloalkyl ester compound such as ethyl bromopropionate (where Y is bromo, n is 1, $R^3$ and $R^4$ are hydrogen, and R is ethyl).

In step 2, hydroxy ester compound e is dehydrated by treatment with acid such as para-toluenesulfonic acid, to yield an unsaturated ester compound f. In certain embodiments the dehydration of step 2 may occur spontaneously during step 1, and thus step 2 may be omitted.

A reduction reaction takes place in step 3 in which the residual unsaturation in compound f is hydrogenated by treatment with hydrogen in the presence of a suitable platinum or palladium catalyst, to provide ester compound g.

In step 4, the compound g is subject to reduction, followed by alkylsulfonylation, to afford sulfonate compound h. This step may be carried out by treatment of compound g with reducing agent such as lithium aluminum hydride to form an alcohol (not shown), which is then treated with alkylsulfonyl halide such as methanesulfonyl chloride.

Amination of arylsulfonate compound h in step 5 provides amine compound i. This amination in many embodiments may comprise treatment of sulfonate compound h with sodium azide to form an azido compound (not shown), which is then reduced, using lithium aluminum hydride or like reducing agent, followed by acid workup to yield amine i.

As in the case of Scheme A, many variations on the procedure of Scheme B are possible and will suggest themselves to those skilled in the art. In on such variation, sulfonate compound h may be treated with cyanide to form a nitrile compound, which in turn is reduced to provide an amine.

The amine group of compound d of Scheme A or compound i of Scheme B may undergo various reactions to provide a variety of $R^2$ functional groups, as shown in Scheme C.

Utility

The compounds of the invention have selective affinity for 5-HT receptors, including the 5-HT$_6$ the 5-HT$_2$A receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also

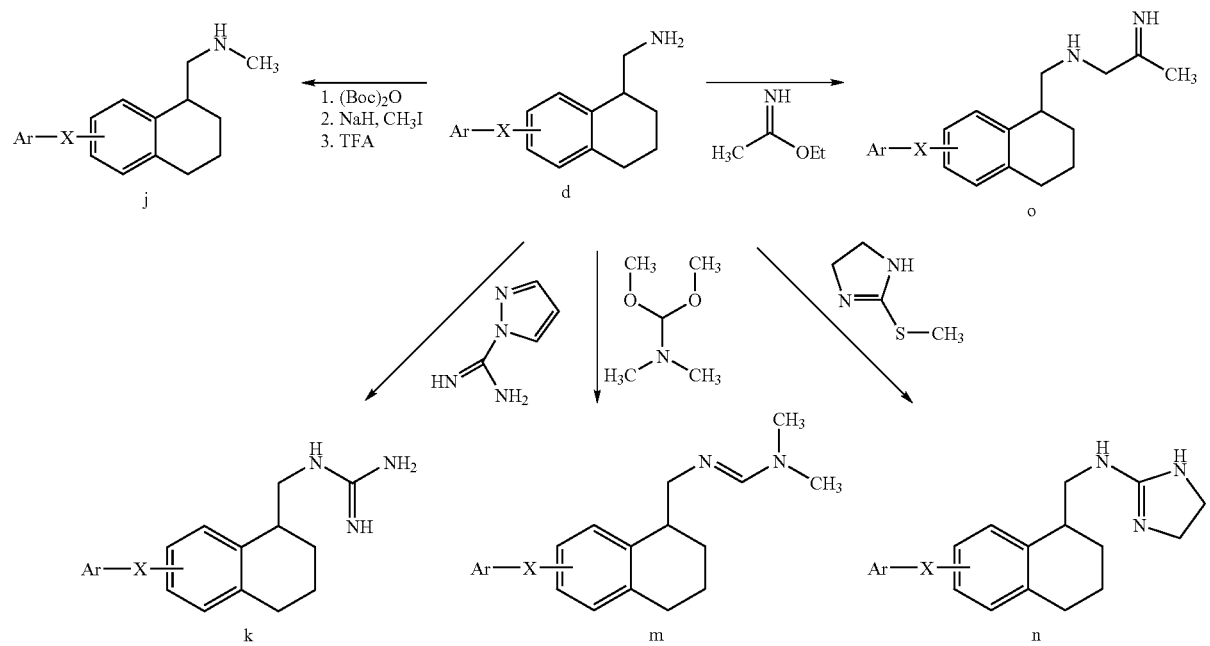

SCHEME C

In Scheme B, compound d may be Boc protected, then subject to alkylation, followed by deprotection to afford methylamino compound j. Compound e may be subject to another alkylation (not shown) to afford the corresponding dimethylamino or other dialkylamino compound.

Compound d may also be reacted with 1H-pyrazol-1-carboxamidine hydrochloride in the presence of amine catalyst under polar aprotic solvent conditions to afford guanidine compound k. Alternatively, compound d may be reacted with dimethylformamide dimethyl acetal to yield formamidine compound m. As yet another alternative, compound d may be treated with 2-methylsulfanyl-4,5-dihydro1H-imidazole to afford imidazolinylamino compound n. In still another alternative, compound d may be reacted with ethyl imidate (acetimidic acid ethyl ester) to provide acetamidine compound o.

Many variations on the procedures of Scheme A, Scheme B and Scheme C are possible and will be readily apparent to those skilled in the art. Specific examples of such additional reactions are provided in the Examples below.

expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described in the Examples below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| DCM | dichloromethane/methylene chloride |
| DDQ | 2,3-dichloro-5,6-dicyano-1,4-benzoquinone |
| DMF | N,N-dimethylformamide |
| DMAP | 4-dimethylaminopyridine |
| EtOAc | ethyl acetate |
| EtOH | ethanol |
| tBuOH | tert-butanol |
| gc | gas chromatography |
| HMPA | hexamethylphosphoramide |
| hplc | high performance liquid chromatography |
| mCPBA | m-chloroperbenzoic acid |
| MeCN | acetonitrile |
| NMP | N-methyl pyrrolidinone |
| TEA | triethylamine |
| TFA | trifluoroacetic acid |
| THF | tetrahydrofuran |
| LDA | lithium diisopropylamine |
| TLC | thin layer chromatography |

Additional procedures for making compounds of the invention are found in U.S. patent application Ser. No. 11/315,706, filed on Dec. 21 2005, the disclosure of which is incorporated herein by reference.

Example 1

N-(5-Aminomethyl-5,6,7,8-tetrahydro-naphthalen-2-yl)-benzenesulfonamide

The synthetic procedure described in this Example was carried out according to the process shown in Scheme C.

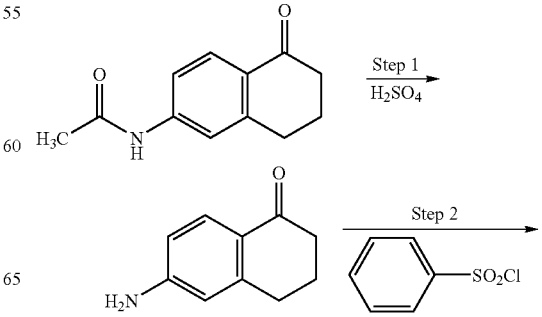

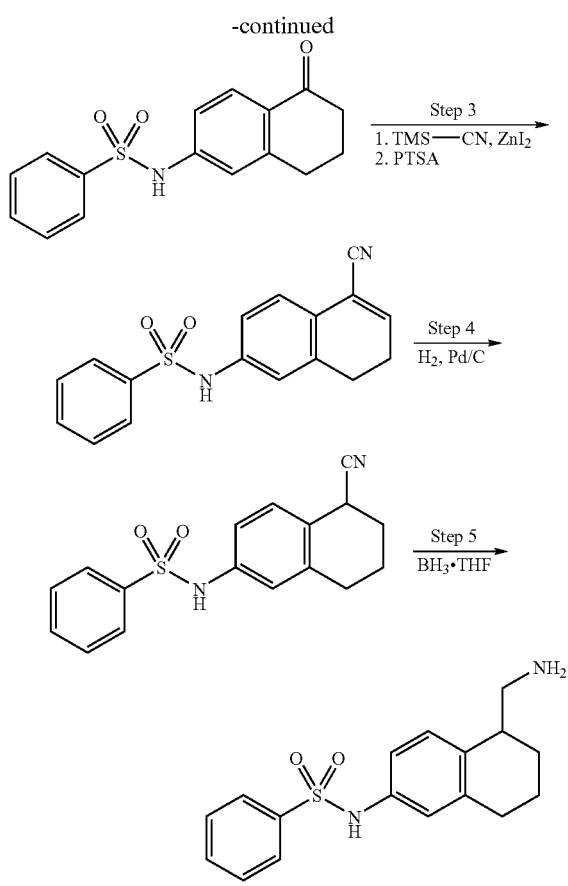

Step 1 6-amino-3,4-dihydro-2H-naphthalen-1-one

A mixture of 2.5 grams (12.3 mmole) N-(5-oxo-5,6,7,8-tetrahydronaphthalen-2-yl)-acetamide in 20 mL 20% sulfuric acid was heated at 90° for 45 minutes. The solution was allowed to cool to room temperature, whereupon 6-amino-3,4-dihydro-2H-naphthalen-1-one sulfate precipitated as a solid mass. The solids were collected by filtration, washed with cold water and dried to give 1.92 g (97%) of 6-amino-3,4-dihydro-2H-naphthalen-1-one sulfate.

Step 2 N-(5-oxo-5,6,7,8-tetrahydro-naphthalen-2-yl)-benzenesulfonamide

To a solution of 0.46 gram (2.85 mmole) 6-amino-3,4-dihydro-2H-naphthalen-1-one in 25 mL pyridine was added 0.605 grams (3.42 mmoles) benzenesulfonyl chloride. The reaction mixture was stirred at 23° C. for 24 hours. The mixture was diluted with 100 mL water and extracted with 200 mL ethyl acetate. The organic phase was dried (magnesium sulfate) and concentrated under reduced pressure. The residue was subjected to low pressure column chromatography over silica gel 230-400 mesh eluting with 50% ethyl acetate in hexane. The title compound was obtained as a solid, 0.48 gram (56%), m.p. 164-165° C., M−H=300.

Step 3 N-(5-Cyano-7,8-dihydro-naphthalen-2-yl)-bezenesulfonamide

N-(5-oxo-5,6,7,8-tetrahydro-naphthalen-2-yl)-benzenesulfonamide (4.21 g, 14 mmol), trimethylsilyl cyanide (10.0 g, 100 mmol) and Zinc Iodide (0.25 g) were combined and stirred under nitrogen for 15 hours. The reaction mixture was then diluted by addition of 200 mL of $Et_2O$, washed with cold water, and the organic layer was dried ($MgSO_4$) and evaporated under reduced pressure to an oil. The oil was dissolved in 250 mL of toluene, and 0.5 g of paratoluene sulfonic acid was added. The reaction mixture was refluxed for three hours, cooled, and the the solvent was removed under reduced pressure. The crude product was eluted through silica under medium pressure with 5% EtOAc in hexanes to yield 1.89 g (6.1 mmol, 44%) of N-(5-Cyano-7,8-dihydro-naphthalen-2-yl)-bezenesulfonamide as an oil. MS: 311 $(M+H)^+$.

Step 4 N-(5-Cyano-5,6,7 8-tetrahydro-naphthalen-2-yl)-benzenesulfonamide

N-(5-Cyano-7,8-dihydro-naphthalen-2-yl)-bezenesulfonamide (5.27 g, 17.2 mmol), 70 mL EtOH, and 50 mL acetic acid were placed in a Parr vessel, and 1.0 g of 10% Palladium on carbon (Fluka Chemica Co.) was added. The reaction mixture was shaken for 15 hours under 55 psi hydrogen. The Parr vessel was purged with nitrogen and the reaction mixture was filtered. The filtrate was added to 500 mL, water, and the aqueous mixture was extracted with EtOAc. The combined organic layers were dried ($MgSO_4$) and evaporated to yield 4.85 g (15.5 mmol, 90%) of N-(5-Cyano-5,6,7,8-tetrahydro-naphthalen-2-yl)-benzenesulfonamide as an oil. MS: 314 $(M+H)^+$.

Step 5 N-(5-Aminomethyl-5,6,7,8-tetrahydro-naphthalen-2-yl)-benzenesulfonamide N-(5-Cyano-5,6,7,8-tetrahydro-naphthalen-2-yl)-benzenesulfonamide(4.85 g, 15.5 mmol) was dissolved in 100 mL of dry tetrahydrofuran (THF), and the mixture was stirred while cooling in an ice bath. Borane-THF complex (40 mL, 1.0M) was added to the cold, stirring solution, and the reaction mixture was stirred under nitrogen for 15 hours at room temperature. The reaction mixture was quenched by addition of 20 mL of 20% HCl and 60 mL of methanol. The solvents were removed under reduced pressure, and the aqueous residue was treated dropwise with 1M NaOH until basic. The residue was extracted with EtOAc and the combined organic layers were dried ($MgSO_4$) and evaporated. The crude product was acidified with dilute HCl in EtOH and recrystallized from EtOAc to yield 2.8 g of N-(5-aminomethyl-5,6,7,8-tetrahydro-naphthalen-2-yl)-benzenesulfonamide as a hydrochloride salt. MS: 317 $(M^+H)^+$.

Similarly prepared, but using 3-fluorobenzensulfonyl chloride in step 2, was N-(5-aminomethyl-5,6,7,8-tetrahydro-naphthalen-2-yl)-3-fluoro-benzenesulfonamide MS: 335 $(M^+H)^+$.

Example 2

3-Fluoro-N-(5-methylaminomethyl-5,6,7,8-tetrahydro-naphthalen-2-yl)-benzenesulfonamide The synthetic procedure described in this Example was carried out according to the process shown in Scheme D.

SCHEME D

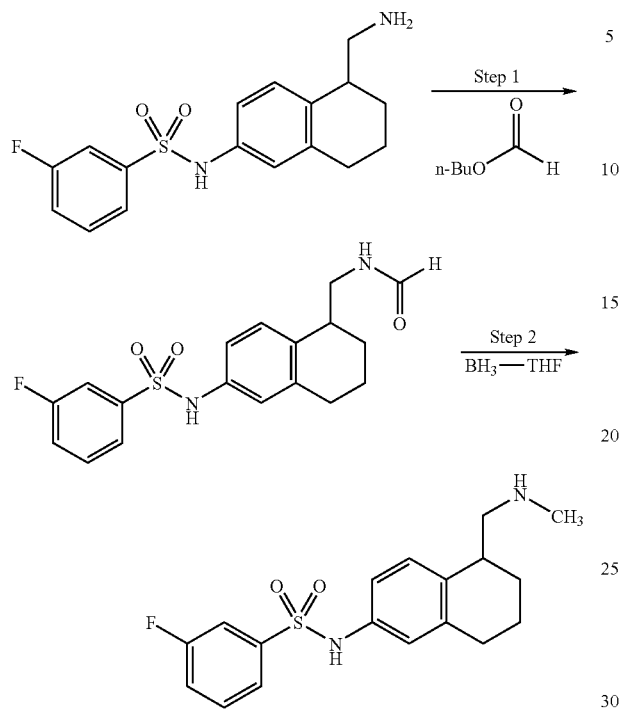

Step 1 3-Fluoro-N-(5-formylaminomethyl-5,6,7,8-tetrahydro-naphthalen-2-yl)-benzenesulfonamide A solution of 0.28 grams (0.837 mmoles) N-(5-aminomethyl-5,6,7,8-tetrahydro-naphthalen-2-yl)-3-fluoro-benzenesulfonamide in 6 mL n-butyl formate was heated under reflux for 1.5 hours. The solution was concentrated under reduced pressure. 3-Fluoro-N-(5-formylaminomethyl-5,6,7,8-tetrahydro-naphthalen-2-yl)-benzenesulfonamide was obtained by recrystallization of the residue from 2-propanol/ethyl ether to provide 0.27 grams (89%) of 3-fluoro-N-(5-formylaminomethyl-5,6,7,8-tetrahydro-naphthalen-2-yl)-benzenesulfonamide, m.p. 143-144° C., M⁺H=363

Step 2 3-Fluoro-N-(5-methylaminomethyl-5,6,7,8-tetrahydro-naphthalen-2-yl)-benzenesulfonamide To a solution of 0.17 grams (0.469 mmoles) 3-fluoro-N-(5-formylaminomethyl-5,6,7,8-tetrahydro-naphthalen-2-yl)-benzenesulfonamide in 5 mL THF was added 2 mL 1.0M borane-THF. The reaction mixture was stirred at 23° C. for 18 hours. 1.0 mL 6N hydrochloric acid was added and the mixture was heated under reflux for 15 minutes. The solution was concentrated under reduced pressure and the residue was partitioned between ethyl acetate and saturated aqueous sodium bicarbonate. The organic phase was dried (magnesium sulfate) and concentrated under reduced pressure. 3-Fluoro-N-(5-methylaminomethyl-5,6,7,8-tetrahydro-naphthalen-2-yl)-benzenesulfonamide was isolated as the crystalline oxalate salt, 0.05 grams (24%), m.p. 135-136° C., M⁺H=349.

Similarly prepared was N-(5-Aminomethyl-5,6,7,8-tetrahydro-naphthalen-2-yl)-benzenesulfonamide oxalate. M⁺H=317.

Example 3

N-[6-(3-Fluoro-benzenesulfonylamino)-1,2,3,4-tetrahydro-naphthalen-1-ylmethyl]-acetamide

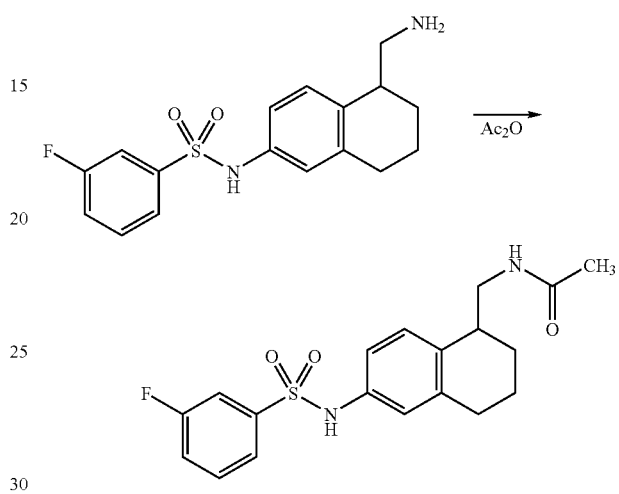

To a solution of 0.18 grams (0.538 mmoles) N-(5-aminomethyl-5,6,7,8-tetrahydro-naphthalen-2-yl)-3-fluoro-benzenesulfonamide in 25 mL pyridine was added 0.052 grams (0.511 mmole) acetic anhydride. The reaction mixture was stirred at 23° C. for 4 hours. The mixture was diluted with water and extracted with ethyl acetate. The organic phase was washed with 0.5M hydrochloric acid, water, and saturated aqueous sodium chloride. The organic phase was dried (magnesium sulfate) and concentrated under reduced pressure. N-[6-(3-Fluoro-benzenesulfonylamino)-1,2,3,4-tetrahydro-naphthalen-1-ylmethyl]-acetamide was obtained as a crystalline solid from ethyl acetate/ethyl ether, 0.18 grams (89%), m.p. 136-137° C., M⁺H=377.

Similarly prepared was R-N-[6-(3-Fluoro-benzenesulfonylamino)-1,2,3,4-tetrahydro-naphthalen-1-ylmethyl]-acetamide, M⁺H=377.

Example 4

3-Fluoro-N-(5-ureidomethyl-5,6,7,8-tetrahydro-naphthalen-2-yl)-benzenesulfonamide

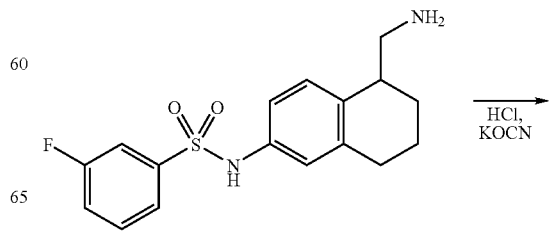

-continued

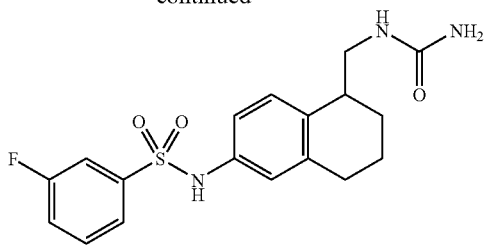

A mixture of 0.23 grams (0.688 mmoles) N-(5-aminomethyl-5,6,7,8-tetrahydro-naphthalen-2-yl)-3-fluoro-benzenesulfonamide, 0.15 mL 6M hydrochloric acid, and 0.112 grams (1.38 mmole) potassium cyanate in 25 mL water was heated under reflux for 1.5 hours. The solid precipitate was collected by filtration and dried in vacuo to provide 3-fluoro-N-(5-ureidomethyl-5,6,7,8-tetrahydro-naphthalen-2-yl)-benzenesulfonamide as a white solid, 0.21 gram (81%), m.p. 162-163° C., M$^+$H=378.

Example 5

N-(5-Aminomethyl-5,6,7,8-tetrahydro-naphthalen-2-yl)-3-fluoro-N-methyl-benzenesulfonamide

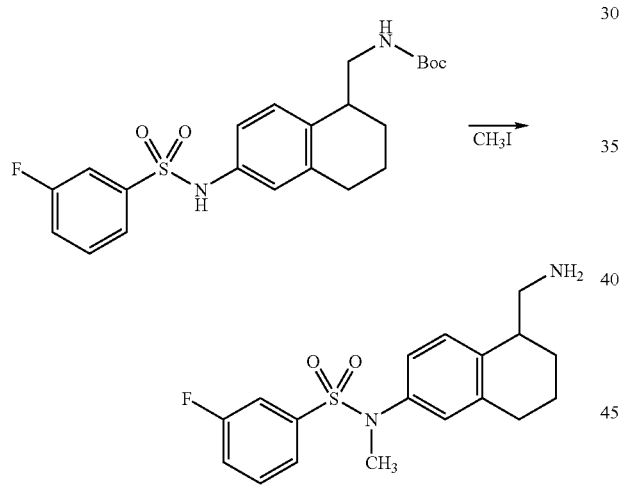

To a solution of 0.22 grams (0.524 mmole) (+/−)-[6-(3-fluoro-benzenesulfonylamino)-1,2,3,4-tetrahydro-naphthalen-1-ylmethyl]-carbamic acid tert-butyl ester in 10 mL DMF was added 0.08 grams (0.576 mmole) potassium carbonate and 0.033 mL (0.524 mmole) iodomethane. The reaction mixture was stirred at 23° C. for 0.5 hours. The mixture was diluted with water and extracted with ethyl acetate. The organic phase was washed with water saturated aqueous sodium chloride, dried (magnesium sulfate) and concentrated under reduced pressure. The residue was dissolved in 3 mL warm TFA and immediately concentrated under reduced pressure. The residue was partitioned between saturated aqueous sodium carbonate ethyl acetate. The organic phase was dried (magnesium sulfate) and concentrated under reduced pressure. N-(5-Aminomethyl-5,6,7,8-tetrahydro-naphthalen-2-yl)-3-fluoro-N-methyl-benzenesulfonamide was isolated as the crystalline oxalate salt, 0.06 grams (18%), m.p. 176-177° C., M$^+$H=349.

Example 6

(R)-5-Aminomethyl-5,6,7,8-tetrahydro-naphthalene-2-sulfonic acid (3-fluoro-phenyl)-amide The synthetic procedure described in this Example was carried out according to the process shown in Scheme E.

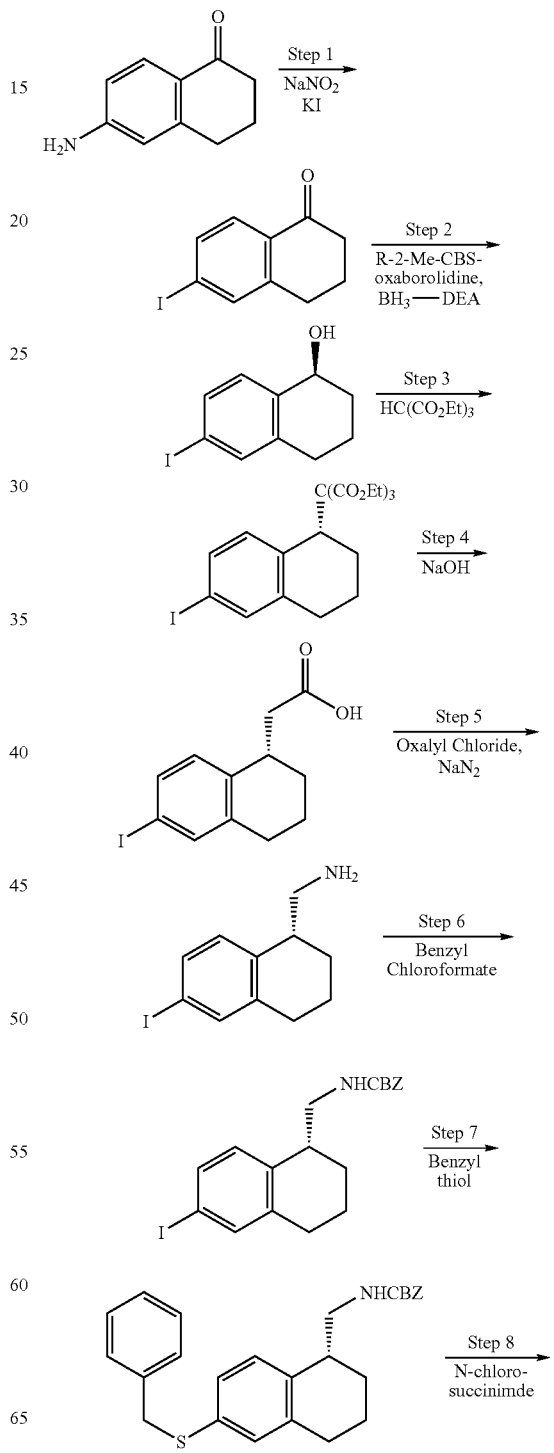

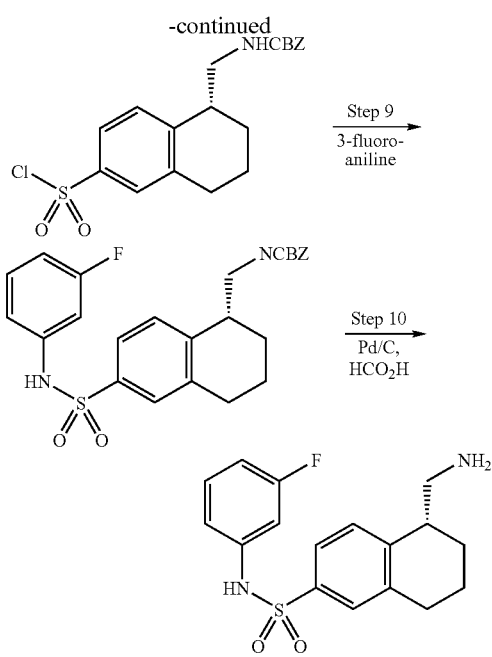

Step 1 6-Iodo-3,4-dihydro-2H-naphthalen-1-one

To 1.92 g (11.9 mmol) 6-amino-3,4-dihydro-2H-naphthalen-1-one sulfate was added 20 mL water and 20 mL glacial acetic acid. The resulting solution was stirred in an ice bath and a solution of 1.72 grams (25 mmoles) sodium nitrite in 15 mL water was added dropwise over 0.5 hour. The reaction mixture was slowly poured into a well stirred solution of 8 grams (48 mmoles) potassium iodide in 80 mL water. The mixture was extracted with diethyl ether, and the organic phase was washed with water, saturated aqueous sodium hydrogen sulfite, and saturated aqueous sodium chloride. The organic phase was dried (magnesium sulfate) and concentrated under reduced pressure. The residue was subjected to low pressure column chromatography over silica gel 230-400 mesh eluting with 5% ethyl acetate in hexane. 6-Iodo-3,4-dihydro-2H-naphthalen-1-one was obtained as a white solid, 3.12 grams (94%), m.p. 77-78°.

Step 2 S-6-Iodo-1,2,3,4-tetrahydro-naphthalen-1-ol

A solution of 3.7 mL (3.7 mmoles) 1.0 M R-2-methyl-CBS-oxazaborolidine in toluene and 7.5 mL (42 mmoles) borane-diethylaniline complex in 40 mL toluene was heated to 30°. A solution of 10 grams (36.8 mmoles) 6-iodo-3,4-dihydro-2H-naphthalen-1-one in 40 mL toluene was added dropwise over 2.5 hours. The reaction mixture was stirred for an additional 0.5 hour at 30°. To the solution (at room temperature) was added 20 mL methanol. After 0.25 hour, 50 mL 1N hydrochloric acid was added slowly. The mixture was stirred for 20 minutes, then was extracted with diethyl ether. The organic phase was washed with 1N aqueous hydrochloric acid, water, and saturated aqueous sodium chloride. The organic phase was dried (magnesium sulfate) and concentrated under reduced pressure. The oily residue was recrystallized from hot hexane. When crystallization was complete, the white solid was collection and dried to give S-6-Iodo-1,2,3,4-tetrahydro-naphthalen-1-ol, 9.62 grams (95%). m.p. 102-103°, $M^+=274$, $[\alpha]_D=+12.20°$ (c=1, chloroform).

Step 3 R-2-Ethoxycarbonyl-2-(6-iodo-1,2,3,4-tetrahydro-naphthalen-1-yl)-malonic acid diethyl ester To a solution of 9.5 grams (34.7 mmoles) S-6-iodo-1,2,3,4-tetrahydro-naphthalen-1-ol and 16 grams (69.3 mmoles) triethylmethane tricarboxylate in 150 mL toluene was added 70 mL 1.0M trimethylphosphine in toluene. The solution was stirred and cooled to −50° under nitrogen. Neat diisopropylazodicarboxylate (14 mL, 69.3 mmoles) was added dropwise over 0.5 hour. The solution was concentrated under reduced pressure. To the residue was added 100 mL water and 100 mL 3N sodium hydroxide. The mixture was extracted with diethyl ether, and the organic phase was washed with 3N aqueous sodium hydroxide, water, 1N aqueous hydrochloric acid, water, and saturated aqueous sodium chloride. After drying (magnesium sulfate) the solution was concentrated under reduced pressure. To the residue was added 25 mL diethyl ether. After 10 minutes the crystalline deposit of diisopropyl-1,2-hydrazinedicarboxylate was removed by filtration. The filtrate was concentrated under reduced pressure and the residue was subjected to low pressure column chromatography over 230-400 mesh silica gel eluting with 7% ethyl acetate in hexane. The title compound was obtained as a white crystalline solid (from hexane), 14.84 grams (88%), m.p. 86-87°, $[\alpha]_D=-20.3°$ (c=1, chloroform), $M^+=488$.

Step 4 S-6-Iodo-1,2,3,4-tetrahydro-naphthalen-1-yl acetic acid

To a solution of 14 grams (28.7 mmoles) R-2-ethoxycarbonyl-2-(6-iodo-1,2,3,4-tetrahydro-naphthalen-1-yl)-malonic acid diethyl ester in 25 mL methanol was added 60 mL water and 60 mL 3N sodium hydroxide. The reaction mixture was heated under reflux for 20 hours, then cooled and concentrated under reduced pressure. To the residue was added 200 mL glacial acetic acid. The solution was heated under reflux for 3 hours, and then it was concentrated under reduced pressure. The residue was partitioned between water and diethyl ether. The organic phase was dried (magnesium sulfate) and concentrated under reduced pressure. The residue was recrystallized from ethyl ether/hexane to give S-6-iodo-1,2,3,4-tetrahydro-naphthalen-1-yl acetic acid, 7.6 grams (84%), m.p. 90-91°, $M^+=316$, $[\alpha]_D=+20°$ (c=1, chloroform).

Step 5 R-C-(6-Iodo-1,2,3,4-tetrahydro-naphthien-1-yl)-methylamine hydrochloride To a solution of 28.4 grams (90 mmoles) S-6-iodo-1,2,3,4-tetrahydro-naphthalen-1-yl acetic acid in 350 mL dichloromethane was added 5 drops DMF and 12 mL (.135 mole) oxalyl chloride. The reaction mixture was stirred at 23° for 1 hour and then it was concentrated under reduced pressure. The residue was dissolved in 250 mL acetone and the solution was cooled to 0°. A solution of 12 grams (0.18 mole) sodium nitrite in 80 mL water was added dropwise over 0.5 hour. The reaction mixture was diluted with 400 mL water and 200 mL saturated sodium chloride. The mixture was extracted with toluene, and the organic phase was dried (magnesium sulfate), then heated under reflux for 0.5 hour. The solution was concentrated under reduced pressure. The residue was dissolved in 150 mL dioxane and the solution was added dropwise to a boiling solution of 250 mL concentrated aqueous hydrochloric acid over 40 minutes. The solution was decanted from a small amount of tar and the warm decantate was concentrated under reduced pressure. The residue was recrystallized from ethanol/ethyl ether to provide R-C-(6-Iodo-1,2, 3,4-tetrahydro-naphthlen-1-yl)-methylamine as the hydrochloride salt, 23.3 grams (80%), m.p. 276-277°, M+=287, [α]$_D$=−2.8° (c=1, methanol).

Step 6 R-(6-Iodo-1,2,3,4-tetrahydro-naphthalen-1-ylmethyl)-carbamic acid benzyl ester To a stirred mixture of 1.0 gram (3.1 mmoles) R-C-(6-iodo-1,2,3,4-tetrahydro-naphthlen-1-yl)-methylamine hydrochloride in 20 mL toluene and 20 mL water was added 1.0 gram (9.4 mmoles) sodium carbonate and 0.5 mL benzyl chloroformate. The reaction mixture was stirred at 23° C. for 2 hours, then diluted with water and extracted with ethyl acetate. The organic phase was dried (magnesium sulfate) and concentrated under reduced pressure. R-(6-Iodo-1,2,3,4-tetrahydro-naphthalen-1-ylmethyl)-carbamic acid benzyl ester was obtained as a crystalline solid from hexane, 1.24 gram (94%), m.p. 111-112° C., M+=421, [α]$_D$=+21.20 (c=1, chloroform).

Step 7 R-(6-Benzylsulfanyl-1,2,3,4-tetrahydro-naphthalen-1-ylmethyl)-carbamic acid benzyl ester Following the general procedure of Itoh and Mase, Organic Letters 6(24): 4587 (2004), 0.52 gram (1.29 mmoles) R-(6-iodo-1,2,3,4-tetrahydro-naphthalen-1-ylmethyl)-carbamic acid benzyl ester, 0.059 gram (0.064 mmoles) tris(dibenzylideneacetone)dipalladium(0), 0.074 gram (0.128 mmoles) 4,5-bis(diphenylphosphino)-9,9-dimethylxanthene, 0.333 gram (2.58 mmoles) diisopropylethyl amine and 0.2 gram (1.42 mmoles) benzyl thiol were added to 15 mL dioxane. The reaction mixture was stirred at 50° for 1 hour. The mixture was diluted with 50 mL diethyl ether and filtered. The filtrate was washed with water, dried (magnesium sulfate) and concentrated under reduced pressure. The residue was subjected to low pressure column chromatography over silica gel 230-400 mesh eluting with 10% ethyl acetate in hexane. The eluted product was recrystallized from hexane to provide R-(6-Benzylsulfanyl-1,2,3,4-tetrahydro-naphthalen-1ylmethyl)-carbamic acid benzyl ester, 0.46 gram (90%), m.p. 82-83°, M+=417.

Step 8 R-(6-Chlorosulfonyl-1,2,3,4-tetrahydro-naphthalen-1-ylmethyl)-carbamic acid benzyl ester To a solution of 0.2 gram (0.48 mmole) R-(6-benzylsulfanyl-1,2,3,4-tetrahydro-naphthalen-1ylmethyl)-carbamic acid benzyl ester in 10 mL 90% aqueous acetic acid was added 0.192 gram (1.44 mmole) N-chlorosuccinimide. The reaction mixture was stirred at 23° C. for 2 hours, then concentrated under reduced pressure and the residue was partitioned between ethyl acetate and water. The organic phase was dried (magnesium sulfate) and concentrated under reduced pressure. The residue was subjected to low pressure column chromatography over silica gel 230-400 mesh eluting with 15% ethyl acetate in hexane. R-(6-Chlorosulfonyl-1,2,3,4-tetrahydro-naphthalen-1-ylmethyl)-carbamic acid benzyl ester was obtained as a heavy oil, 0.17 gram (90%), M+H=394.

Step 9 R-[6-(3-Fluoro-phensulfamoyl)-1,2,3,4-tetrahydro-naphthalen-1-ylmethyl]-carbamic acid benzyl ester A solution of 0.13 gram (0.33 mmole) R-(6-chlorosulfonyl-1,2,3,4-tetrahydro-naphthalen-1-ylmethyl)-carbamic acid benzyl ester and 0.04 gram (0.35 mmole) 3-fluoroaniline in 5 mL pyridine was stirred at 23° C. for 1 hour. The solution was concentrated under reduced pressure and the residue was partitioned between ethyl acetate and 0.1N aqueous hydrochloric acid. The organic phase was washed with 0.1N aqueous hydrochloric acid and water, dried (magnesium sulfate) and concentrated under reduced pressure to leave R-[6-(3-fluoro-phensulfamoyl)-1,2,3,4-tetrahydro-naphthalen-1-yl-methyl]-carbamic acid benzyl ester as a homogenous white foam, 0.15 gram (97%), M+H=469.

Step 10 (R)-5-Aminomethyl-5,6,7,8-tetrahydro-naphthalene-2-sulfonic acid (3-fluoro-phenyl)-amide To a stirred mixture of 0.12 gram (0.26 mmole) R-[6-(3-fluoro-phensulfamoyl)-1,2,3,4-tetrahydro-naphthalen-1-yl-methyl]-carbamic acid benzyl ester and 0.032 gram 10% palladium on carbon in 6 mL methanol was added 0.2 mL 97% formic acid. The reaction mixture was stirred at 23° C. for 1 hour, then filtered and concentrated under reduced pressure. (R)-5-Aminomethyl-5,6,7,8-tetrahydro-naphthalene-2-sulfonic acid (3-fluoro-phenyl)-amide was obtained as a crystalline solid from methanol/ethyl acetate/ethyl ether, 0.069 gram (70%), m.p. 122-123° C., M+H=335.

Similarly prepared were C-[6-(2,3-Dihydro-indole-1-sulfonyl)-1,2,3,4-tetrahydro-naphthalen-1-yl]-methylamine (M+H=343) and C-[6-(3,4-Dihydro-2H-quinoline-1-sulfonyl)-1,2,3,4-tetrahydro-naphthalen-1-yl]-methylamine (M+H=357).

Example 7

R-N-(5-Aminomethyl-5,6,7,8-tetrahydro-naphthalen-2-yl)-3-fluoro-benzenesulfonamide The synthetic procedure described in this Example was carried out according to the process shown in Scheme F.

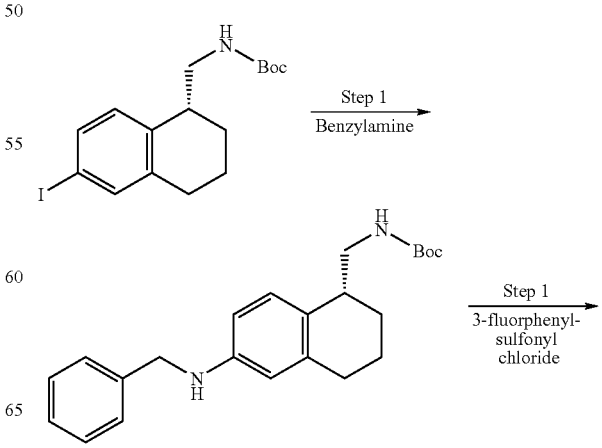

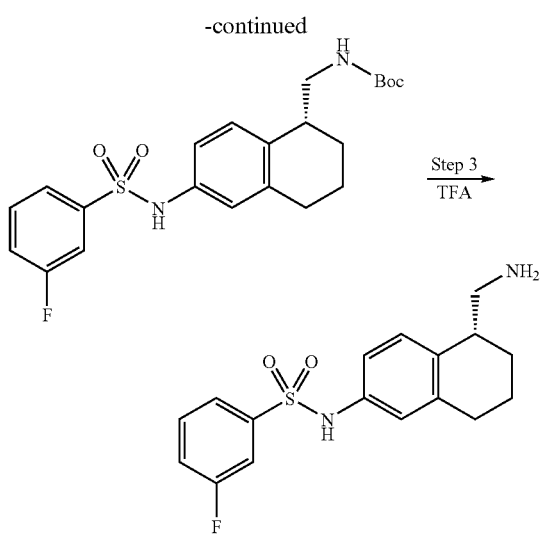

Step 1 R-(6-Benzylamino-1,2,3,4-tetrahydro-naphthalen-1-ylmethyl)-carbamic acid tert-butyl ester.

This step follows the general procedure of Zhang, Cai and Ma, J. Organic Chemistry 70(13): 5164-5173 (2005). A mixture of 0.73 grams (1.9 mmole) R-(6-iodo-1,2,3,4-tetrahydro-naphthlen-1-ylmethyl)-arbamic acid tert-butyl ester, 0.036 gram (0.19 mmole) copper (I) iodide, 0.044 gram (0.38 mmole) L-proline and 0.31 gram (2.85 mmole) benzylamine in 2 mL DMSO was heated at 60° C. for 44 hours. The reaction mixture was diluted with 15 mL water and extracted with diethyl ether. The organic phase was washed with water and saturated aqueous sodium chloride. The organic phase was dried (magnesium sulfate) and concentrated under reduced pressure. The residue was subjected to column chromatography over silica gel 230-400 mesh eluting with a gradient of 5-20% ethyl acetate in hexane. The title compound was obtained as a solid, 0.29 grams (40%).

Step 2 R-[6-(3-Fluoro-benzenesulfonylamino)-1,2,3,4-tetrahydro-naphthalen-1-ylmethyl]-carbamic acid tert-butyl ester A mixture of 0.37 grams (0.97 mmoles) R-(6-benzylamino-1,2,3,4-tetrahydro-naphthalen-1-ylmethyl)-carbamic acid tert-butyl ester and 0.1 gram Pearlman's catalyst (20% palladium (II) hydroxide on carbon) in 8 mL methanol containing 0.06 grams (1.0 mmole) glacial acetic acid was stirred under 1 atmosphere hydrogen gas at 23° C. for 1 hour. The mixture was filtered and the filtrate was concentrated under reduced pressure. The oily residue was dissolved in a mixture of 3 mL THF and 1.5 mL pyridine. To this mixture was added 0.21 grams (1.1 mmole) 3-fluoro-phenylsulfonyl chloride, and the reaction mixture was stirred at 23° C. for 3.5 hours. The mixture was concentrated to one half volume under reduced pressure and partitioned between ethyl acetate and 5% aqueous hydrochloric acid. The organic phase was washed with water and saturated aqueous sodium chloride, dried (magnesium sulfate) and concentrated under reduced pressure. The residue was subjected to column chromatography over silica gel 230-400 mesh eluting with 2% methanol in chloroform. R-[6-(3-Fluoro-benzenesulfonylamino)-1,2,3,4-tetrahydro-naphthalen-1-ylmethyl]-carbamic acid tert-butyl ester was isolated as a solid, 0.4 grams (95%).

Step 3 R-N-(5-Aminomethyl-5 6,7,8-tetrahydro-naphthalen-2-yl)-3-fluoro-benzenesulfonamide To a stirred suspension of 0.4 gram (0.92 mmole) R-[6-(3-fluoro-benzenesulfonylamino)-1,2,3,4-tetrahydro-naphthalen-1-ylmethyl]-carbamic acid tert-butyl ester in 6 mL dichloromethane was added 2 mL TFA. The mixture was stirred at 23° C. for 1 hour and then concentrated under reduced pressure. The residue was partitioned between ethyl acetate and 0.75 M aqueous sodium carbonate. The organic phase was dried (magnesium sulfate) and concentrated under reduced pressure. R-N-(5-Aminomethyl-5,6,7,8-tetrahydro-naphthalen-2-yl)-3-fluoro-benzenesulfonamide was obtained a solid by recrystallization from ethanol/ethyl ether/hexane, 0.24 gram (78%), m.p. 142-144° C., M⁺H=335.

Example 8

N-(6-Benzenesulfonylamino-1,2,3,4-tetrahydro-naphthalen-1-ylmethyl)-acetamidine

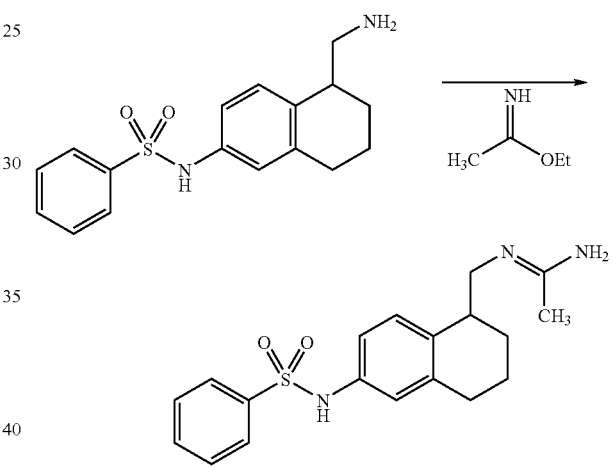

N-(5-Aminomethyl-5,6,7,8-tetrahydro-naphthalen-2-yl)-benzenesulfonamide and ethyl imidate (acetimidic acid ethyl ester) are dissolved in absolute ethanol, and the reaction mixture is stirred under argon at room temperature. Solvent is removed under reduced pressure, and the residue is recrystallized from Et₂O/EtOH to give N-(6-Benzenesulfonylamino-1,2,3,4-tetrahydro-naphthalen-1-ylmethyl)-acetamidine. N-(6-Phenylsulfamoyl-1,2,3,4-tetrahydro-naphthalen-1-ylmethyl)-acetamidine may be similarly prepared.

Example 9

N-(5-Guanidinomethyl-5,6,7,8-tetrahydro-naphthalen-2-yl)-benzenesulfonamide

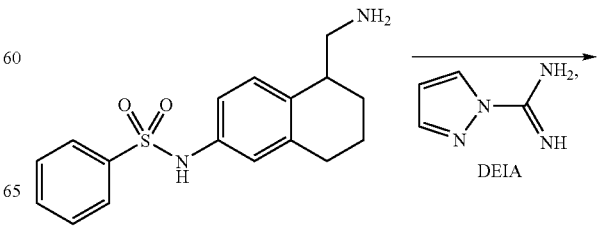

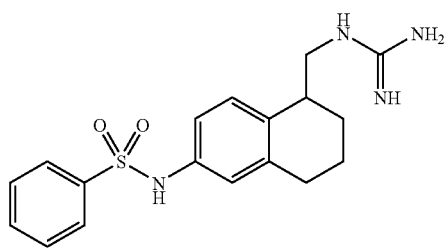

N-(5-Aminomethyl-5,6,7,8-tetrahydro-naphthalen-2-yl)-benzenesulfonamide, 1H-pyrazol-1-carboxamidine hydrochloride and diethyl isopropylamine are dissolved in DMF, and the reaction mixture is heated to 100° C., then cooled and diluted by addition of of water. The aqueous mixture is extracted with EtOAc, and the combined organic layers are dried over $MgSO_4$, filtered, and concentrated under reduced pressure to give N-(5-Guanidinomethyl-5,6,7,8-tetrahydro-naphthalen-2-yl)-benzenesulfonamide. 5-Guanidinomethyl-5,6,7,8-tetrahydro-naphthalene-2-sulfonic acid phenylamide may be similarly prepared.

Example 10

N-{5-[(4,5-Dihydro-1H-imidazol-2-ylamino)-methyl]-5,6,7,8-tetrahydro-naphthalen-2-yl}-benzene sulfonamide

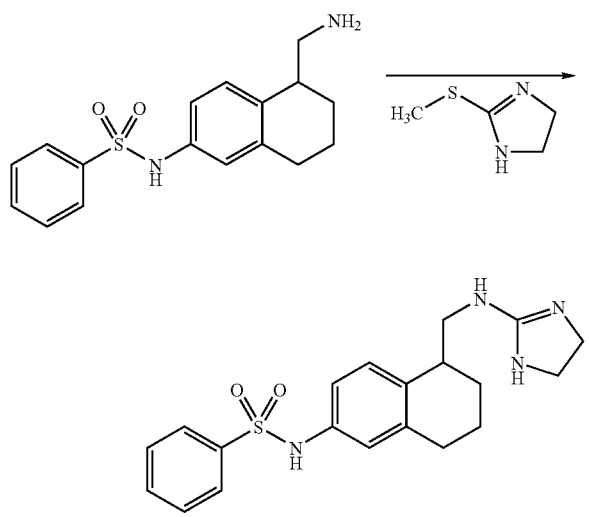

N-(5-Aminomethyl-5,6,7,8-tetrahydro-naphthalen-2-yl)-benzenesulfonamide and 2-methylsulfanyl-4,5-dihydro-1H-imidazole hydroiodide were added to methylene chloride and the reaction mixture was heated to reflux until all of the solvent evaporates. The reaction mixture is heated to 150° C. and then cooled. The resulting mixture is basified by dropwise addition of aqueous NaOH solution, and then purified by preparative liquid chromatography to give N-{5-[(4,5-Dihydro-1H-imidazol-2-ylamino)-methyl]-5,6,7,8-tetrahydro-naphthalen-2-yl}-benzenesulfonamide. 5-[(4,5-Dihydro-1H-imidazol-2-ylamino)-methyl]-5,6,7,8-tetrahydro-napthalene-2-sulfonic acid phenylamide may be similarly prepared.

Example 11

N-{5-[(5,5-Dimethyl-1,4,5,6-tetrahydro-pyrimidin-2-ylamino)-methyl]-5,6,7,8-tetrahydro-naphthalen-2-yl}-benzenesulfonamide

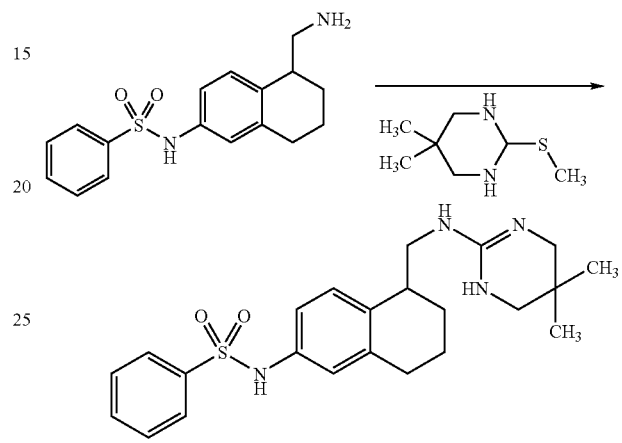

N-(5-Aminomethyl-5,6,7,8-tetrahydro-naphthalen-2-yl)-benzenesulfonamide is prepared from 7-Benzenesulfonyl-3,4-dihydro-2H-naphthalen-1-one following the procedures of Examples 1 and 2. C-(6-Benzenesulfonyl-naphthalen-1-yl)-methylamine and 5,5-dimethyl-2-methylsulfanyl-hexahydro-pyrimidine hydrochloride are added to methylene chloride, and the reaction mixture is heated to gentle reflux until all of the solvent is evaporated. The reaction mixture is heated to 150° C. and then cooled. The resulting mixture is basified by dropwise addition of aqueous NaOH solution, and then purified by preparative liquid chromatography to give N-{5-[(5,5-Dimethyl-1,4,5,6-tetrahydro-pyrimidin-2-ylamino)-methyl]-5,6,7,8-tetrahydro-naphthalen-2-yl}-benzenesulfonamide. 5-[(5,5-Dimethyl-1,4,5,6-tetrahydro-pyrimidin-2-ylamino)-methyl]-5,6,7,8-tetrahydro-naphthalene-2-sulfonic acid phenylamide may be similarly prepared.

Example 12

N-[5-(Dimethylamino-methyleneaminomethyl)-5,6,7,8-tetrahydro-naphthalen-2-yl]-benzenesulfonamide

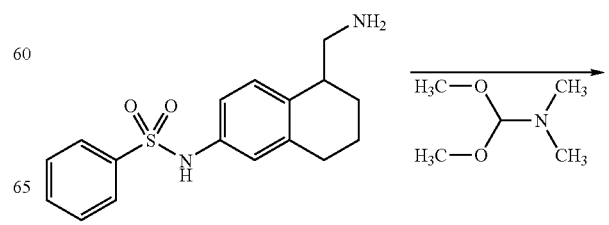

-continued

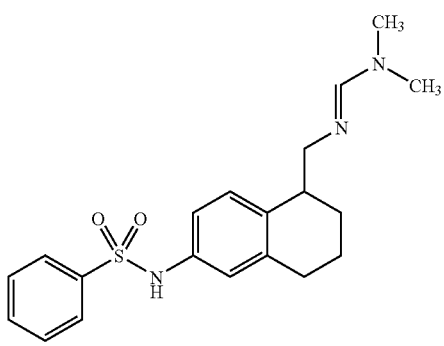

N-(5-Aminomethyl-5,6,7,8-tetrahydro-naphthalen-2-yl)-benzenesulfonamide is added to dimethylformamide dimethyl acetal, and the reaction mixture is heated to 95° C. The reaction mixture is cooled and quenched by addition of water, and the resulting aqueous mixture is extracted with EtOAc. The organic layer is washed with water, brine, dried (MgSO$_4$), and evaporated under reduced pressure to give N'-(6-Benzenesulfonylamino-1,2,3,4-tetrahydro-naphthalen-1-ylmethyl)-N,N-dimethyl-acetamidine. N,N-Dimethyl-N'-(6-phenylsulfamoyl-1,2,3,4-tetrahydro-naphthalen-1-ylmethyl)-acetamidine may be similarly prepared.

Example 13

N-(5-Dimethylaminomethyl-naphthalen-2-yl)-benzenesulfonamide

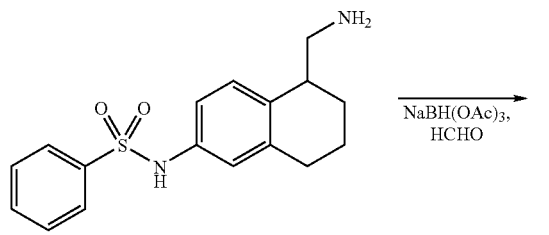

Using the procedure described Journal of Organic Chemistry, 61(11), 3849-3862 (1996), a solution of N-(5-Aminomethyl-5,6,7,8-tetrahydro-naphthalen-2-yl)-benzenesulfonamide and aqueous formaldehyde in methylene is stirred at room temperature, and NaBH(OAc)$_3$ is added and the reaction mixture is stirred at room temperature. Saturated aqueous NaHCO$_3$ is slowly added to quench the reaction, and the aqueous mixture is extracted with EtOAc. The organic layer is washed with water and brine, dried (MgSO$_4$), filtered, and concentrated under reduced pressure to afford N-(5-Dimethylaminomethyl-naphthalen-2-yl)-benzenesulfonamide. 5-Dimethylaminomethyl-naphthalene-2-sulfonic acid phenylamide may be similarly prepared.

Example 14

N-{5-[(5-Oxo-4,5-dihydro-1H-imidazol-2-ylamino)-methyl]-naphthalen-2-yl}-benzenesulfonamide

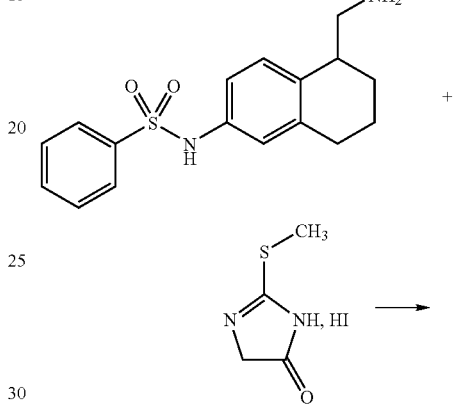

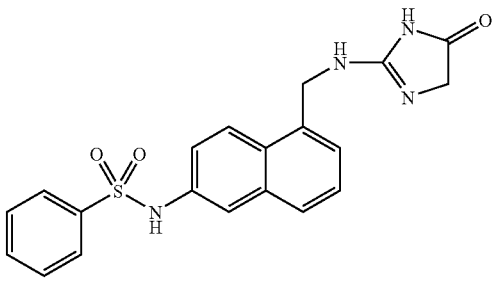

A mixture of N-(5-Aminomethyl-5,6,7,8-tetrahydro-naphthalen-2-yl)-benzenesulfonamide, 2-methylsulfanyl-3,5-dihydro-imidazol-4-one (prepared by the method reported by Chen et al., WO9736859) and sodium hydroxide in ethanol is heated to reflux, then concentrated under reduced pressure, diluted with ethyl acetate, and washed with aqueous sodium carbonate. The organic phase is dried (magnesium sulfate) and concentrated under reduced pressure to give N-{5-[(5-Oxo-4,5-dihydro-1H-imidazol-2-ylamino)-methyl]-naphthalen-2-yl}-benzenesulfonamide. 5-[(5-Oxo-4,5-dihydro-1H-imidazol-2-ylamino)-methyl]-naphthalene-2-sulfonic acid phenylamide may be similarly prepared.

Example 15

N-(6-Benzenesulfonylamino-naphthalen-1-ylmethyl)-2-methylamino-acetamide

The synthetic procedure described in this Example was carried out according to the process shown in Scheme G.

Example 16

2-[(6-Benzenesulfonylamino-nalphthalen-1-ylmethyl)-amino]-N-methyl-acetamide The synthetic procedure described in this Example was carried out according to the process shown in Scheme H.

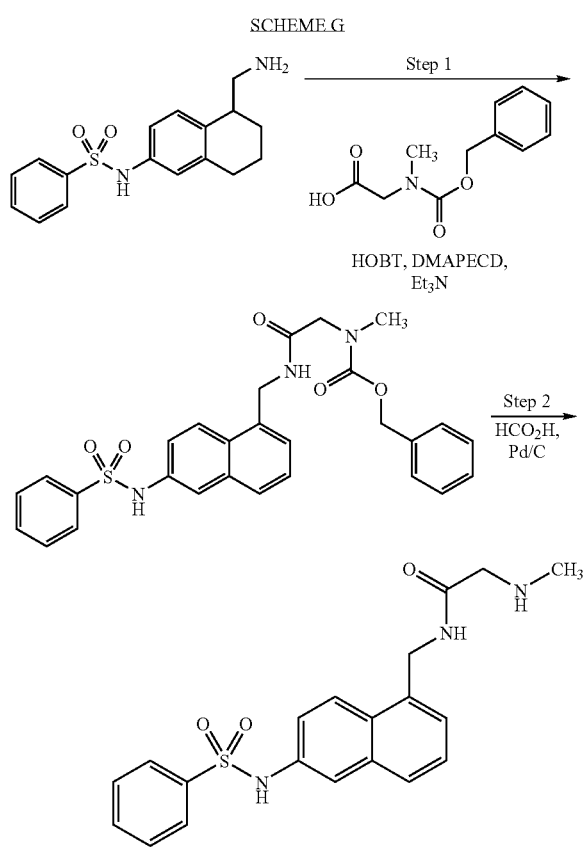

Step 1 {[(6-Benzenesulfonylamino-naphthalen-1-ylmethyl)-carbamoyl]-methyl}-methyl-carbamic acid benzyl ester A mixture of N-(5-Aminomethyl-5,6,7,8-tetrahydro-naphthalen-2-yl)-benzenesulfonamide, (Benzyloxycarbonyl-methyl-amino)-acetic acid, 1-hydroxybenzotriazole, N-(3-dimethylaminopropyl)-N-ethylcarbodiimide and triethylamine in methylene chloride is stirred at room temperature. The reaction is quenched by addition of water, and the mixture is eluted through silica gel to give {[(6-Benzenesulfonylamino-naphthalen-1-ylmethyl)-carbamoyl]-methyl}-methyl-carbamic acid benzyl ester.

Step 2 N-(6-Benzenesulfonylamino-naphthalen-1-ylmethyl)-2-methylamino-acetamide To a stirring solution of {[(6-Benzenesulfonylamino-naphthalen-1-ylmethyl)-carbamoyl]-methyl}-methyl-carbamic acid benzyl ester in methanol and ormic acid at room temperature is added palladium on carbon. The mixture is stirred at room temperature, filtered thru Celite, and the filtrate is concentrated to give N-(6-benzenesulfonyl-naphthalen-1-ylmethyl)-2-methylamino-acetamide. 2-Methylamino-N-(6-phenylsulfamoyl-naphthalen-1-ylmethyl)-acetamide may be similarly prepared.

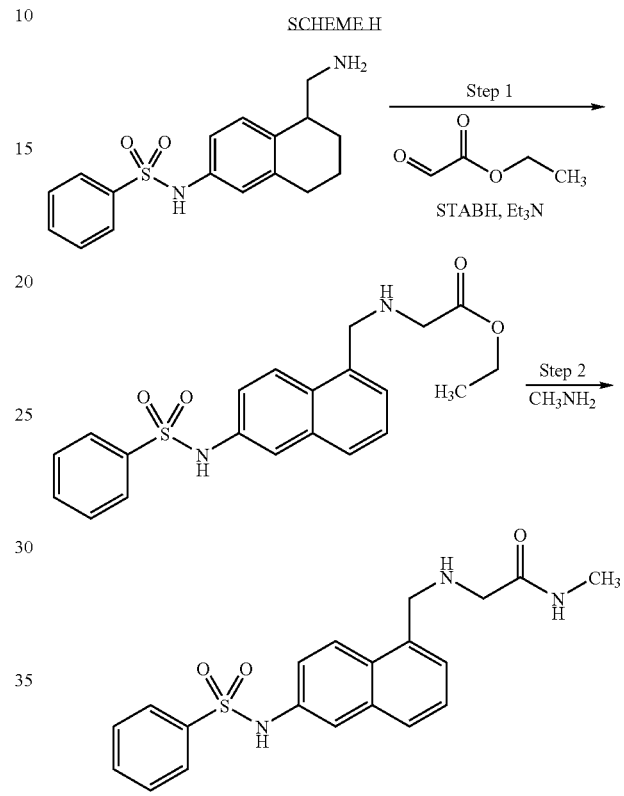

Step 1 [(6-Benzenesulfonylamino-naphthalen-1-ylmethyl)-amino]-acetic acid ethyl ester N-(5-Aminomethyl-5,6,7,8-tetrahydro-naphthalen-2-yl)-benzenesulfonamide and triethyl amine (0.2 ml, 1.55 mmol) in dichloroethane are stirred and cooled in an ice-bath. Ethylgloxylate is added, followed by sodiumtriacetoxyborohydride. The reaction is stirred and then quenched by addition of 2% sodium carbonate solution. The mixture is extracted with ethyl acetate, and the organic layer is dried over magnesium sulfate, filtered, and concentrated under reduced pressure to give [(6-Benzenesulfonylamino-naphthalen-1-ylmethyl)-amino]-acetic acid ethyl ester.

Step 2 2-[(6-Benzenesulfonylamino-naphthalen-1-ylmethyl)-amino]-N-methyl-acetamide

[(6-Benzenesulfonylamino-naphthalen-1-ylmethyl)-amino]-acetic acid ethyl ester is added to methylamine in methanol, and the solution is stirred at room temperature, then concentrated under reduced pressure. The oil is dissolved in ethanol and 1N HCl in diethyl ether is added to precipitate 2-[(6-benzenesulfonyl-naphthalen-1-ylmethyl)-amino]-N-methyl-acetamide as a hydrochloride salt.

Example 17

N-[5-(Methanesulfonylamino-methyl)-naphthalen-2-yl]-benzene sulfonamide

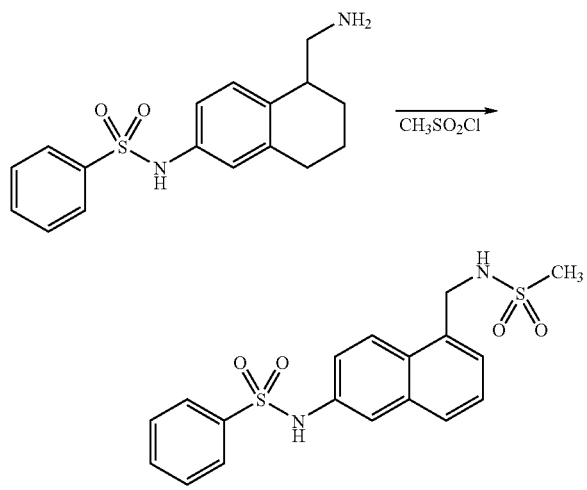

N-(5-Aminomethyl-5,6,7,8-tetrahydro-naphthalen-2-yl)-benzenesulfonamide is dissolved in methylene chloride and pyridine, and the mixture is cooled in an ice bath. Methanesulfonyl chloride is added dropwise, and the reaction mixture is stirred at ice bath temperature, then allowed to warm to room temperature. The reaction mixture is quenched by addition of water and extracted with methylene chloride. The organic layer is washed with water, dried (MgSO$_4$), filtered and concentrated under reduced pressure to give N-[5-(Methanesulfonylamino-methyl)-naphthalen-2-yl]-benzenesulfonamide. 5-(Methanesulfonylamino-methyl)-naphthalene-2-sulfonic acid phenylamide may be similarly prepared.

Example 18

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 19

Radioligand Binding Studies

This example illustrates in vitro radio ligand binding studies of compound of formula I.

The binding activity of compounds of this invention in vitro was determined as follows. Duplicate determinations of 5-HT$_6$ ligand affinity were made by competing for binding of [$^3$H]LSD in cell membranes derived from HEK293 cells stably expressing recombinant human 5-HT$_6$ receptor. Duplicate determinations of 5-HT$_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-HT$_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June; 115(4): 622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT2A receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT2A), filtered onto Packard GF-B plates (pre-soaked with 0.3% PEI) using a Packard 96 well cell harvester and washed 3 times in ice cold 50 mM Tris-HCl.

Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, compounds of Formula I were tested and found to be selective 5-HT$_6$ antagonists, selective 5-HT2A antagonists, or both. For example, the compound N-(5-Methylaminomethyl-5,6,7,8-tetrahydronaphthalen-2-yl)-benzenesulfonamide exhibited a pKi of approximately 9.86 for 5-HT$_6$.

Example 20

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. Behav. Brain Res. 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

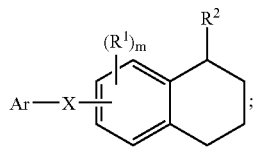

or a pharmaceutically acceptable salt thereof, wherein:

m is 0 to 1;

Ar is phenyl 2-halophenyl or 3-halophenyl;

X is —SO$_2$—NH— or —NH—SO$_2$—;

each R$^1$ is independently halo, alkyl, haloalkyl, alkoxy, hydroxy, heteroalkyl, cyano, —S(O)$_t$—R$^a$, —C(=O)—NR$^b$R$^c$, —SO$_2$—NR$^b$R$^c$, —N(R$^d$)—C(=O)—R$^e$, or —C(=O)—R$^e$, or —C(=O)—R$^e$, where t is from 0 to 2, R$^a$, R$^b$, R$^c$, R$^d$ and R$^e$ each independently is hydrogen or alkyl;

R$^2$ is

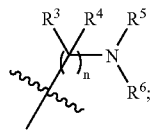

n is 1;

R$^3$ and R$^4$ are hydrogen;

one of R$^5$ and R$^6$ is hydrogen and the other is aminocarbonyl.

2. The compound of claim 1, wherein X is located at the 6-position of the tetralin ring system.

3. The compound of claim 1, wherein said compound is 3-Fluoro-N-(5-ureidomethyl-5,6,7,8-tetrahydro-naphthalen-2-yl)-benzenesulfonamide.

4. A pharmaceutical composition comprising an effective amount of the compound of claim 1 in admixture with a pharmaceutically acceptable carrier.

* * * * *